US007271179B2

(12) United States Patent
Bemis et al.

(10) Patent No.: US 7,271,179 B2
(45) Date of Patent: Sep. 18, 2007

(54) INHIBITORS OF JAK PROTEIN KINASE

(75) Inventors: Guy W. Bemis, Arlington, MA (US); Scott L. Harbeson, Cambridge, MA (US); Mark Ledeboer, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/430,805

(22) Filed: May 6, 2003

(65) Prior Publication Data
US 2004/0038992 A1  Feb. 26, 2004

Related U.S. Application Data

(63) Continuation of application No. PCT/US03/14223, filed on May 6, 2003.

(60) Provisional application No. 60/378,185, filed on May 6, 2002.

(51) Int. Cl.
*C07D 417/02* (2006.01)
*A61K 3/47* (2006.01)
(52) U.S. Cl. .............. 514/312; 514/259; 514/260; 544/284; 546/153
(58) Field of Classification Search ............... 514/259, 514/260, 312; 544/284; 546/153
See application file for complete search history.

(56) References Cited

U.S. PATENT DOCUMENTS 6,232,320 B1 * 5/2001 Stewart et al. ............... 514/301
6,486,158 B1 * 11/2002 Wang et al. ................ 514/248

FOREIGN PATENT DOCUMENTS

| JP | 2001354658 A | 12/2001 |
| WO | WO99/31096 A1 | 6/1999 |
| WO | WO99/62908 A2 | 12/1999 |
| WO | WO 00/51587 A2 | 9/2000 |
| WO | WO 02/00649 A1 | 1/2002 |

OTHER PUBLICATIONS

Sah, Chemical Abstracts 129:54345, abstract of Indian J of Heterocyclic Chemistry, 1998, vol. 7(3), 201-204.*
Misra, Chemical Abstracts 96:85479, abstract of J of the indian Chemical Society, 1981, vol. 58(110, 1118-1119.*
Stewart et al., "Discovery of Inhibitors of Cell Adhesion Molecule Expression in Human Endothelial Cells. 1. Selective Inhibition of ICAM-1 and E-Selectin Expression", J. Med. Chem., 44(6): 988-1002 (2001).
Bobranski et al., "New Purine Derivatives", Archivum Immunologiae Et Therapiae Experimentalis, 22(3):419-432 (1974).
Database Chemcats, Chemical Abstracts Service, Columbus, OH, Database Accession No. 2002:743378, CAS Registry No. 295787-55-2.
Database Chemcats, Chemical Abstracts Service, Columbus, OH, Database Accession No. 2002:738386, CAS Registry No. 295787-56-3.
Database Chemcats, Chemical Abstracts Service, Columbus, OH, Database Accession No. 1998:618096, CAS Registry No. 295787-58-5.
Database Chemcats, Chemical Abstracts Service, Columbus, OH, Database Accession No. 2002:738391, CAS Registry No. 295787-64-3.
Database Chemcats, Chemical Abstracts Service, Columbus, OH, Database Accession No. 2002:738388, CAS Registry No. 295787-59-6.
Database Chemcats, Chemical Abstracts Service, Columbus, OH, Database Accession No. 2002:738387, CAS Registry No. 295787-57-4.
Database Chemcats, Chemical Abstracts Service, Columbus, OH, Database Accession No. 2002:738390, CAS Registry No. 295787-62-1.
Database Chemcats, Chemical Abstracts Service, Columbus, OH, Database Accession No. 2001:2445131, CAS Registry No. 314026-41-0.

* cited by examiner

*Primary Examiner*—Zinna N. Davis
(74) *Attorney, Agent, or Firm*—Karen E. Brown

(57) ABSTRACT

The present invention relates to compounds useful as inhibitors of protein kinases. The invention also provides pharmaceutically acceptable compositions comprising said compounds and methods of using the compositions in the treatment of various disease, conditions, or disorders.

21 Claims, No Drawings

INHIBITORS OF JAK PROTEIN KINASE

CROSS-REFERENCE TO RELATED APPLICATIONS

The present application claims priority under 35 U.S.C. § 120 to Application No. PCT/US03/14223 fled May 6, 2003; which claims priority under 35 U.S.C. § 119(e) to U.S. Provisional Application No. 60/378,185, filed May 6, 2002, entitled "Inhibitors of Jak Protein Kinase", the entire contents of which are hereby incorporated by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J*. 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J*. 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Janus kinases (JAK) are a family of tyrosine kinases consisting of JAK1, JAK2, JAK3 and TYK2. The JAKs play a critical role in cytokine signaling. The downstream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank *Mol. Med.* 1999, 5, 432-456 and Seidel et al., *Oncogene* 2000, 19, 2645-2656].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al., *Blood* 2000, 96, 2172-2180].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al., *Nature* 1990, 346, 274-276 and Galli, N. *Engl. J. Med.* 1993, 328, 257-265]. A crucial role for JAK3 in IgE receptor-mediated mast cell responses in vitro and in vivo has been established [Malaviya et al., *Biochem. Biophys. Res. Commun.* 1999, 257, 807-813]. In addition, the prevention of type I hypersensitivity reactions, including anaphylaxis, mediated by mast cell-activation through inhibition of JAK3 has also been reported [Malaviya et al., *J. Biol. Chem.* 1999 274, 27028-27038]. Targeting mast cells with JAK3 inhibitors modulated mast cell degranulation in vitro and prevented IgE receptor/antigen-mediated anaphylactic reactions in vivo.

A recent study described the successful targeting of JAK3 for immunosuppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 2001, 33, 3268-3270].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner et al., *J. Immunol.* 2000, 164, 3894-3901].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu et al., *Biochem. Biophys. Res. Commun.* 2000, 267, 22-25].

Signal transducer and activator of transcription (STAT) proteins are activated by, among others, the JAK family kinases. Results from a recent study suggested the possibility of intervention in the JAK/STAT signaling pathway by targeting JAK family kinases with specific inhibitors for the treatment of leukemia [Sudbeck et al., *Clin. Cancer Res.* 1999, 5, 1569-1582]. JAK3 specific compounds were shown to inhibit the clonogenic growth of JAK3-expressing cell lines DAUDI, RAMOS, LC1-19, NALM-6, MOLT-3 and HL-60.

In animal models, TEL/JAK2 fusion proteins have induced myeloproliferative disorders and in hematopoietic cell lines, and introduction of TEL/JAK2 resulted in activation of STAT1, STAT3, STAT5, and cytokine-independent growth [Schwaller et al., *EMBO J.* 1998, 17, 5321-5333].

Inhibition of JAK3 and TYK2 abrogated tyrosine phosphorylation of STAT3, and inhibited cell growth of mycosis fungoides, a form of cutaneous T-cell lymphoma. These results implicated JAK family kinases in the constitutively activated JAK/STAT pathway that is present in mycosis fungoides [Nielsen et al., *Proc. Nat. Acad. Sci. U.S.A.* 1997, 94, 6764-6769]. Similarly, STAT3, STAT5, JAK1 and JAK2 were demonstrated to be constitutively activated in mouse T-cell lymphoma characterized initially by LCK overexpression, thus further implicating the JAK/STAT pathway in abnormal cell growth [Yu et al., *J. Immunol.* 1997, 159, 5206-5210]. In addition, IL-6-mediated STAT3 activation was blocked by an inhibitor of JAK, leading to sensitization of myeloma cells to apoptosis [Catlett-Falcone et al., *Immunity* 1999, 10, 105-115].

Accordingly, there is a great need to develop compounds useful as inhibitors of protein kinases. In particular, it would be desirable to develop compounds that are useful as inhibitors of JAK-3, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of JAK-3 protein kinases. These compounds have the general formula I:

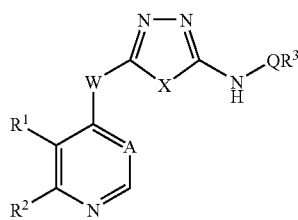

or a pharmaceutically acceptable derivative thereof, wherein A, Q, W, X, $R^1$, $R^2$, and $R^3$ are as defined below.

These compounds, and pharmaceutically acceptable compositions thereof, are useful for treating or lessening the severity of a variety of disorders, including allergic disorders such as asthma and atopic dermatitis, autoimmune diseases such as SLE lupus and psoriasis, and conditions associated with organ transplantation.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention:
The present invention relates to a compound of formula I:

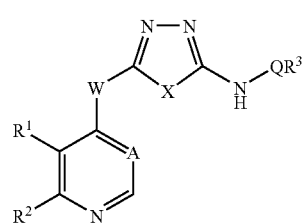

or a pharmaceutically acceptable salt thereof, wherein:
W and X are each independently oxygen or sulfur;
A is nitrogen, CH, C—CN, or C—($C_{1-3}$ aliphatic);
$R^1$ and $R^2$ are taken together to form an optionally substituted 3-7 membered saturated, partially unsaturated, or fully unsaturated ring having 0-3 heteroatoms independently selected from nitrogen, oxygen, or sulfur;
Q is a valence bond, —C(O)—, —C(O)NR—, —C(O)C(O)—, —$CO_2$—, —C(O)$CO_2$—, —$SO_2$—, or an optionally substituted $C_{1-6}$ alkylidene chain, wherein:
  one or two non-adjacent methylene units of Q are optionally and independently replaced by —O—, —S—, —NR—, —C(O)—, —$CO_2$—, —C(O)NR—, —OC(O)NR—, —NRC(O)—, —$NRCO_2$—, —NRC(O)NR—, —S(O)—, —$SO_2$—, —$NRSO_2$—, —$SO_2$NR—, or —$NRSO_2$NR—;
each R is independently hydrogen or an optionally substituted $C_{1-6}$ aliphatic group, wherein:
  two R bound to the same nitrogen atom are optionally taken together with the nitrogen to form an optionally substituted 3-7 membered saturated, partially unsaturated, or fully unsaturated ring having 0-2 heteroatoms, in addition to the nitrogen bound thereto, independently selected from nitrogen, oxygen, or sulfur;
$R^3$ is R or Ar; and
Ar is an optionally substituted ring selected from:
  (a) a 3-8 membered monocyclic or 8-10 membered bicyclic saturated, partially unsaturated, or aryl ring;
  (b) a 3-7 membered heterocyclic ring having 1-3 heteroatoms independently selected from nitrogen, oxygen, or sulfur; or
  (c) a 5-6 membered monocyclic or 8-10 membered bicyclic heteroaryl ring having 1-4 heteroatoms independently selected from nitrogen, oxygen, or sulfur.

2. Compounds and Definitions:
Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O) R°; —NR°C(S)R°; —NR°C(O)N(R°)$_2$; —NR°C(S)N(R°)$_2$; —NR°CO$_2$R°; —NR°NR°C(O)R°; —NR°NR°C(O)N (R°)$_2$; —NR°NR°CO$_2$R°; —C(O) C(O)R°; —C(O)CH$_2$C (O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N (OR°)R°; —C(NOR°)R°; —S(O)$_2$R°; —S(O)$_3$R°; —SO$_2$N (R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O) R° wherein each independent occurrence of R° is selected from hydrogen, optionally substituted $C_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R$^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

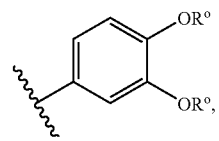

these two occurrences of R° are taken together with the oxygen atoms to which they are bound to form a fused 6-membered oxygen containing ring:

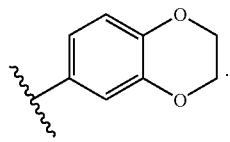

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

3. Description of Exemplary Compounds:

Preferred rings formed by R$^1$ and R$^2$ of formula I are selected from an optionally substituted 5-7 membered saturated, partially unsaturated, or fully unsaturated ring having 0-2 heteroatoms independently selected from nitrogen, oxygen, or sulfur. More preferred optionally substituted rings formed by R$^1$ and R$^2$ are selected from benzo, thieno, cyclohexo, pyrido, tetrahydropyrido, or pyrimido. Preferred substituents on the ring formed by $R^1$ and $R^2$ are selected from halogen, $R^o$, $OR^o$, $N(R^o)_2$, and $SR^o$, wherein $R^o$ is defined generally and in subsets herein. More preferred substituents on the ring formed by $R^1$ and $R^2$ are selected from chloro, bromo, fluoro, Me, Et, $CF_3$, OH, and $OCH_3$.

Preferred Q groups of formula I are selected from a valence bond, —C(O)—, —C(O)NR—, —$CO_2$—, —C(O)$CO_2$—, —$SO_2$—, or a $C_{1-4}$ alkylidene chain wherein one or two non-adjacent methylene units of Q are optionally and independently replaced by —O—, —S—, —NR—, —C(O)—, —$CO_2$—, or —$SO_2$—. More preferred Q groups of formula I are selected from a valence bond, —C(O)—, —C(O)NH—, —$CO_2$—, —C(O)$CO_2$—, —$SO_2$—, —C(O)$CH_2$O—, —C(O) $CH_2$S—, or —C(O)$NHCH_2$—.

Preferred $R^3$ groups of formula I are selected from an optionally substituted $C_{1-6}$ aliphatic group, or an optionally substituted ring selected from:
(a) a 3-6 membered monocyclic saturated or aryl ring;
(b) a 5-6 membered heterocyclic ring having 1-2 heteroatoms independently selected from nitrogen, oxygen, or sulfur; or
(c) a 5-6 membered monocyclic or a 9-10 membered bicyclic heteroaryl ring having 1-3 heteroatoms independently selected from nitrogen, oxygen, or sulfur.

More preferred $R^3$ groups of formula I are optionally substituted groups selected from methyl, ethyl, propyl, isopropyl, isobutyl, tert-butyl, cyclopropyl, cyclopentyl, cyclohexyl, phenyl, pyridyl, thienyl, furanyl, isoxazolyl, triazolyl, benzothienyl, or benzo[1,3]dioxolyl. Preferred substituents on $R^3$, when present, are selected from $R^o$, halogen, $N(R^o)_2$, $OR^o$, or $SR^o$, wherein $R^o$ is defined generally and in subsets herein.

According to one embodiment, the present invention relates to a compound of formula II:

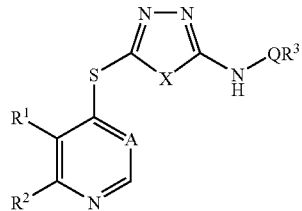

II or a pharmaceutically acceptable salt thereof, wherein A, Q, X, $R^1$, $R^2$, and $R^3$ are as defined above.

Preferred Q, $R^1$, $R^2$, and $R^3$ groups of formula II are as described above for compounds of formula I.

According to another embodiment, the present invention relates to a compound of formula III:

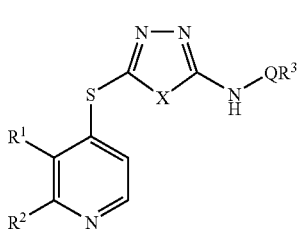

III or a pharmaceutically acceptable salt thereof, wherein Q, X, $R^1$, $R^2$, and $R^3$ are as defined above.

Preferred Q, $R^1$, $R^2$, and $R^3$ groups of formula III are as described above for compounds of formula I.

According to another embodiment, the present invention relates to a compound of formula IV:

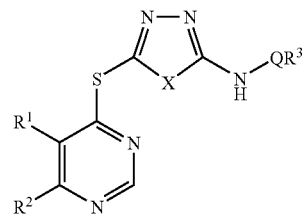

IV or a pharmaceutically acceptable derivative thereof, wherein Q, X, $R^1$, $R^2$, and $R^3$ are as defined above.

Preferred Q, $R^1$, $R^2$, and $R^3$ groups of formula IV are as described above for compounds of formula I.

According to another emobodiment, the present invention relates to a compound of formula II, III, or IV, wherein X is sulfur.

According to another emobodiment, the present invention relates to a compound of formula II, III, or IV, wherein $R^1$ and $R^2$ form a benzo ring.

Representative examples of compounds of formula I are set forth below in Table 1.

TABLE 1

Examples of Compounds of Formula I:

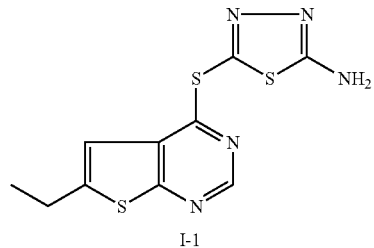

I-1

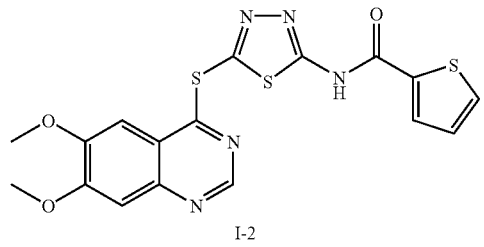

I-2

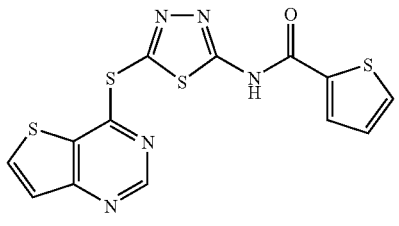

I-3

TABLE 1-continued
Examples of Compounds of Formula I:
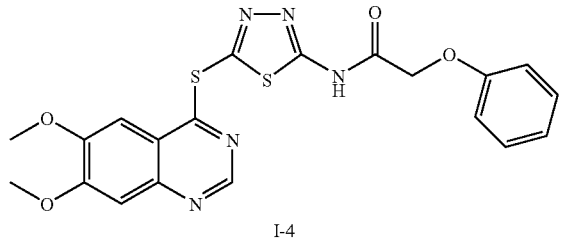
I-4
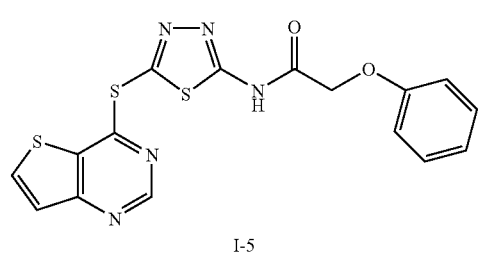
I-5
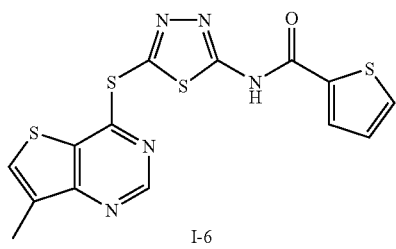
I-6
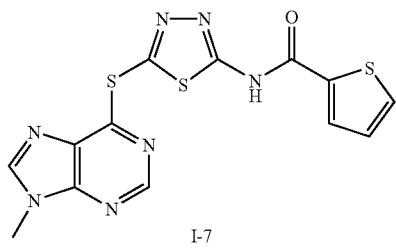
I-7
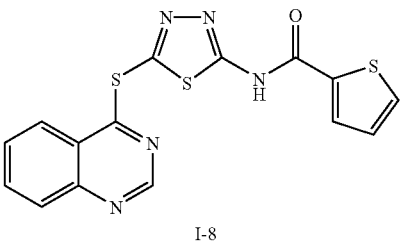
I-8
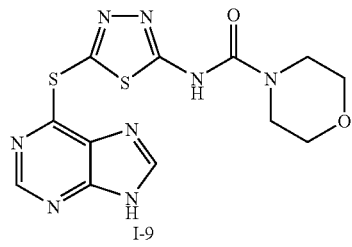
I-9
TABLE 1-continued
Examples of Compounds of Formula I:
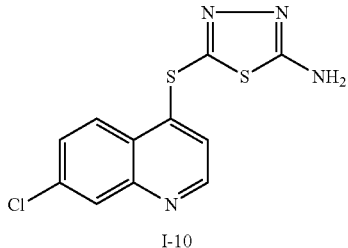
I-10
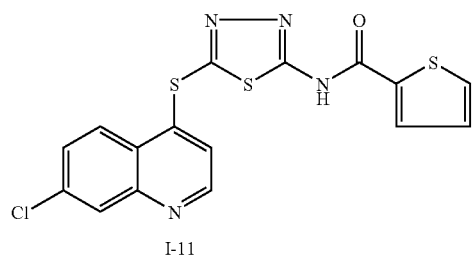
I-11
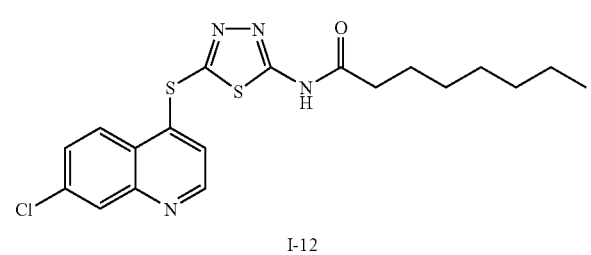
I-12
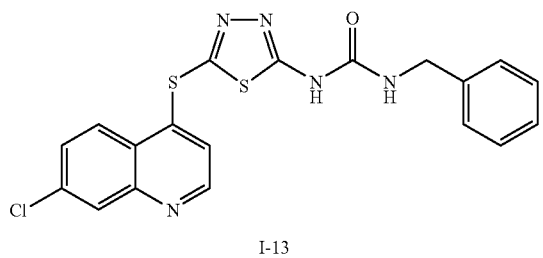
I-13
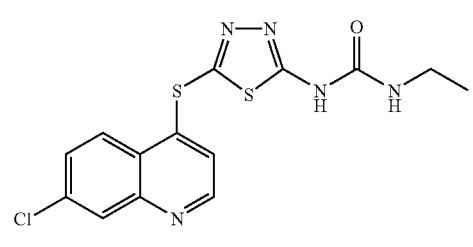
I-14
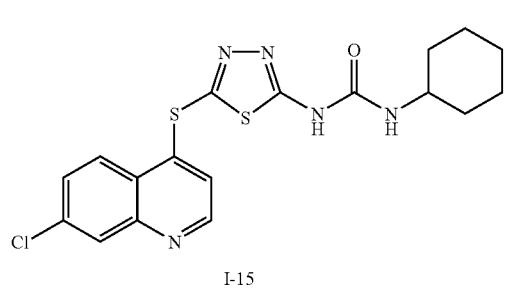
I-15

TABLE 1-continued
Examples of Compounds of Formula I:
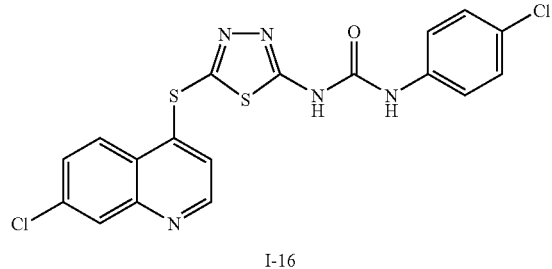
I-16
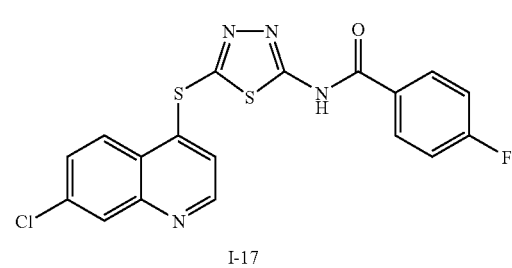
I-17
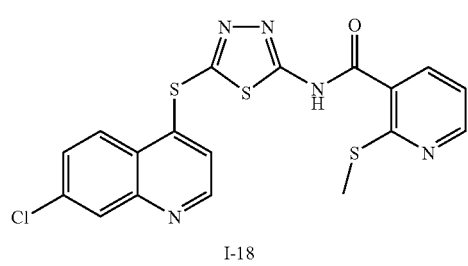
I-18
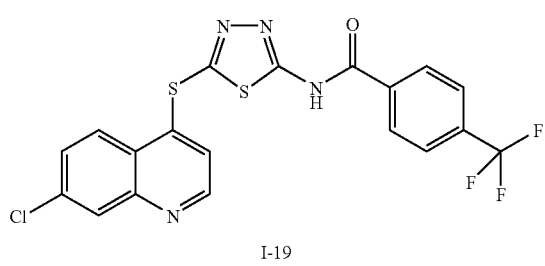
I-19
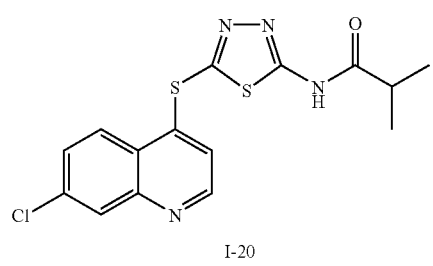
I-20
TABLE 1-continued
Examples of Compounds of Formula I:
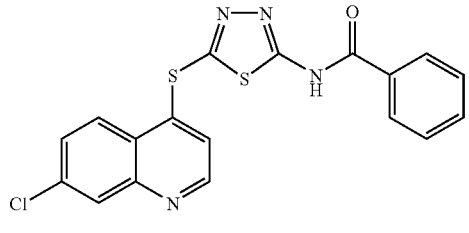
I-21
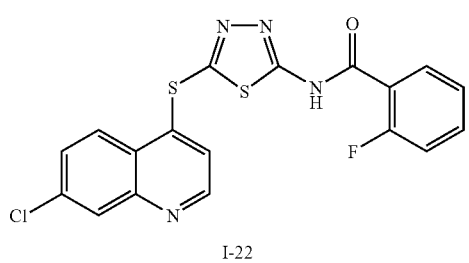
I-22
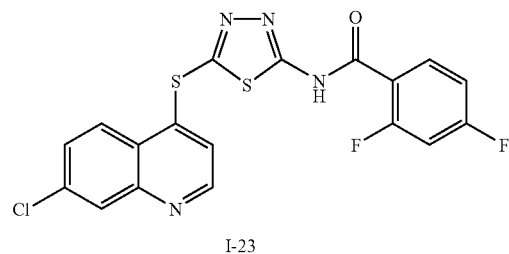
I-23
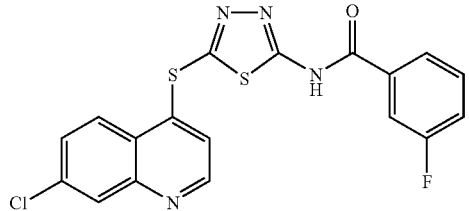
I-24
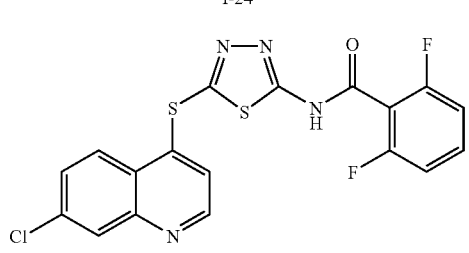
I-25
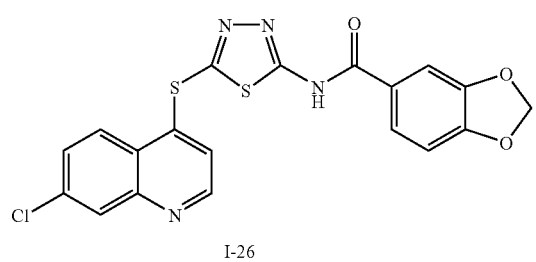
I-26

TABLE 1-continued
Examples of Compounds of Formula I:
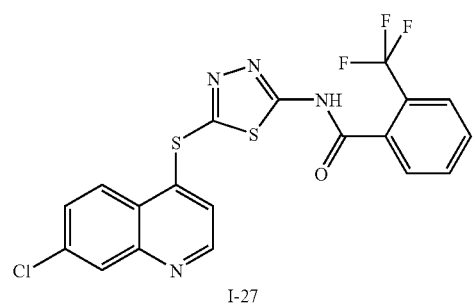
I-27
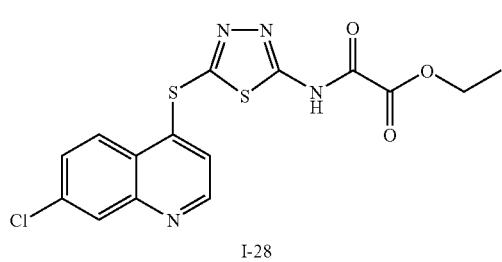
I-28
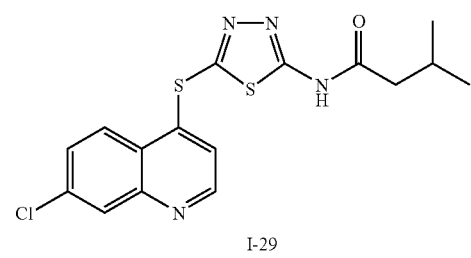
I-29
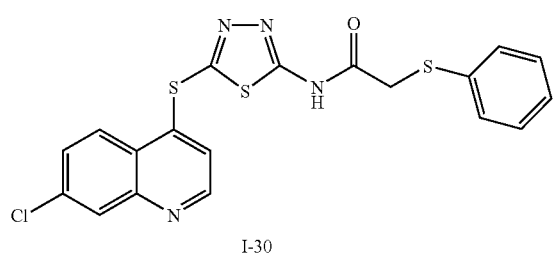
I-30
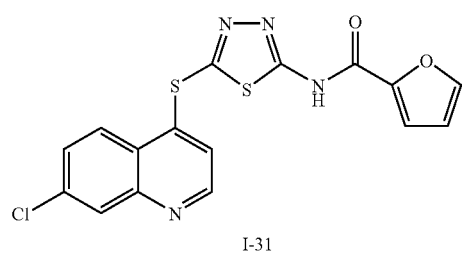
I-31
TABLE 1-continued
Examples of Compounds of Formula I:
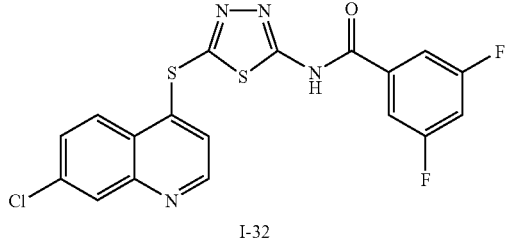
I-32
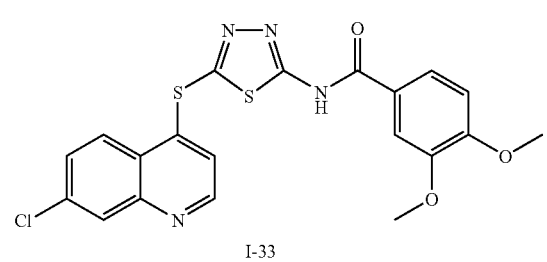
I-33
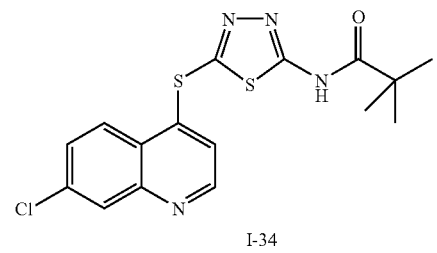
I-34
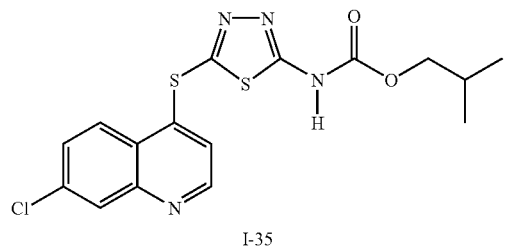
I-35
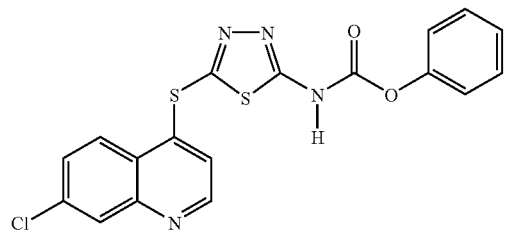
I-36
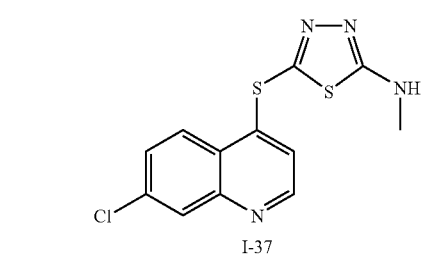
I-37

TABLE 1-continued
Examples of Compounds of Formula I:
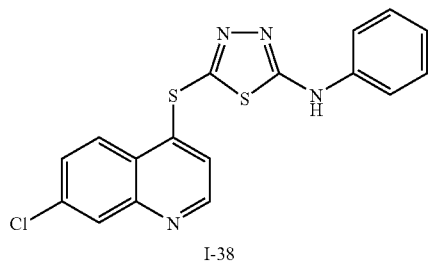
I-38
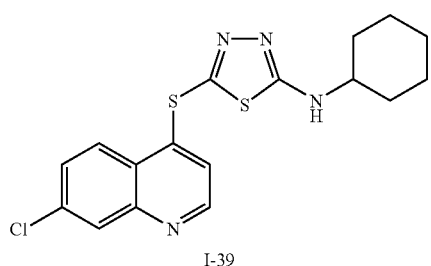
I-39
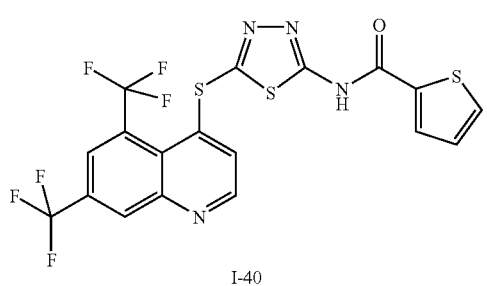
I-40
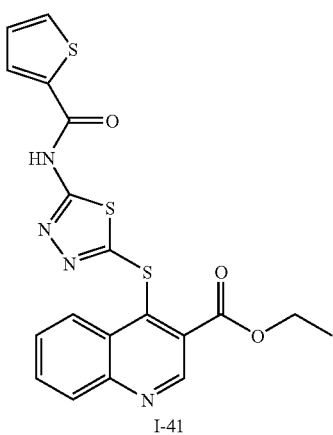
I-41
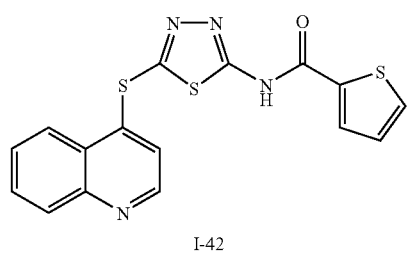
I-42
TABLE 1-continued
Examples of Compounds of Formula I:
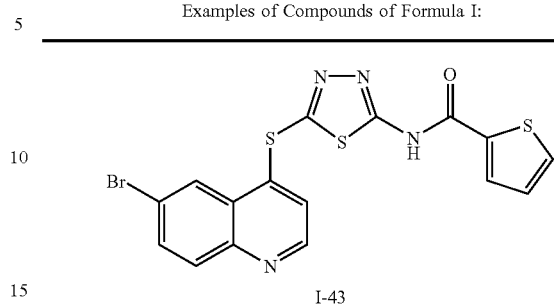
I-43
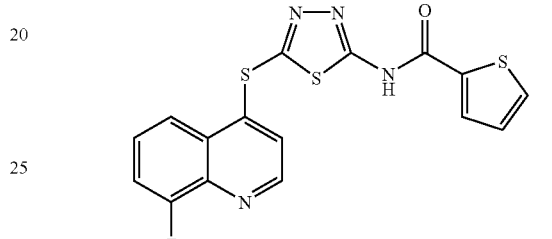
I-44
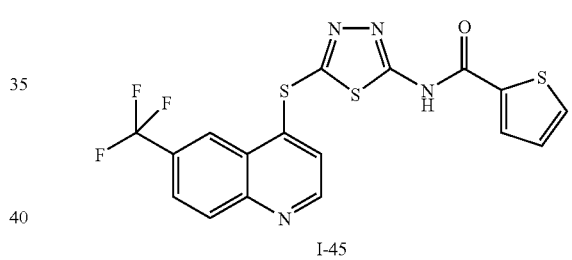
I-45
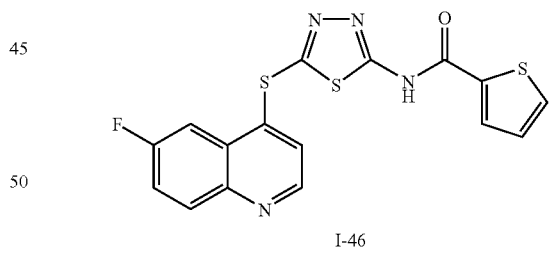
I-46
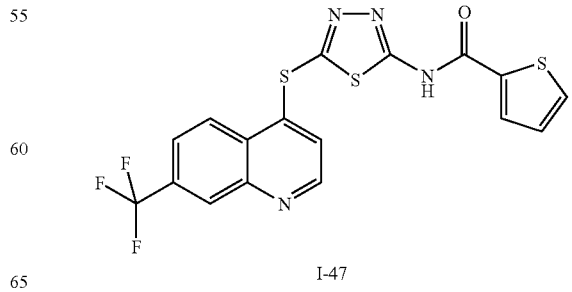
I-47

TABLE 1-continued
Examples of Compounds of Formula I:
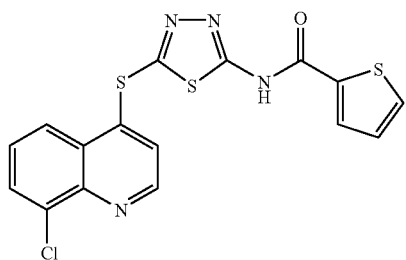
I-48
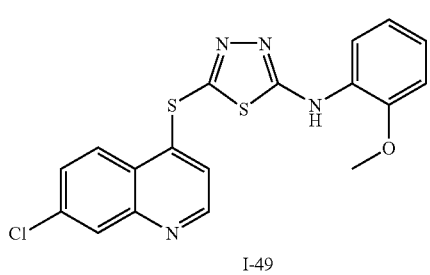
I-49
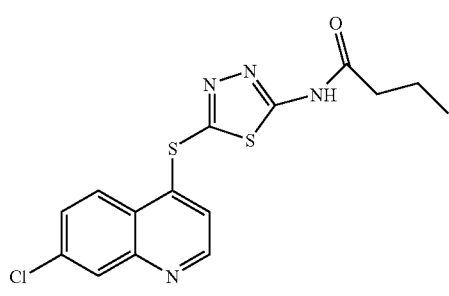
I-50
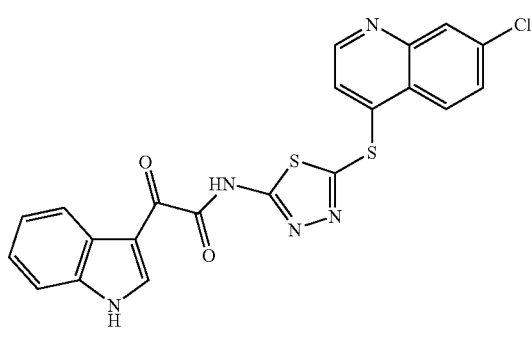
I-51
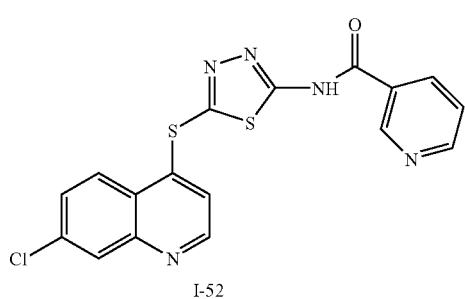
I-52
TABLE 1-continued
Examples of Compounds of Formula I:
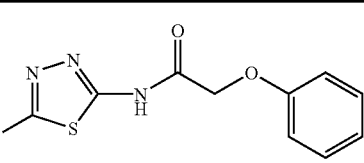
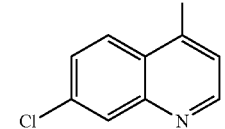
I-53
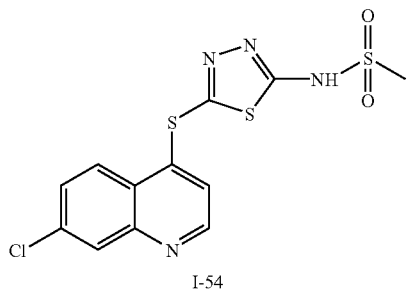
I-54
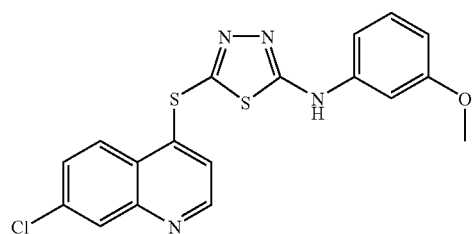
I-55
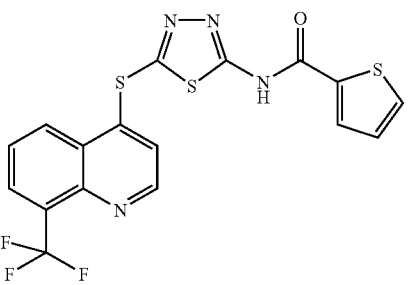
I-56
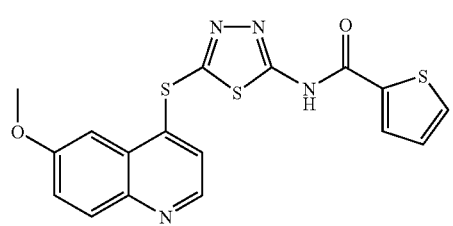
I-57

TABLE 1-continued
Examples of Compounds of Formula I:
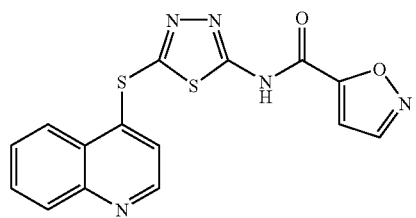
I-58
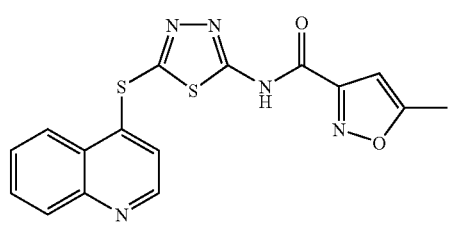
I-59
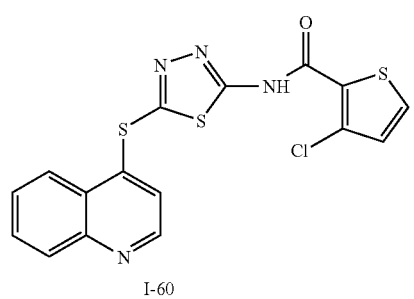
I-60
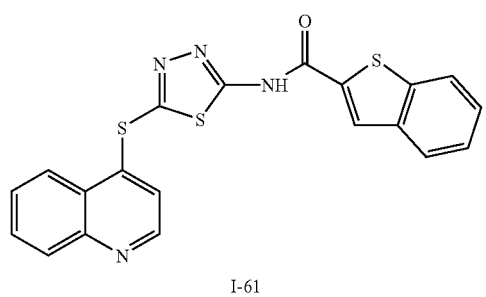
I-61
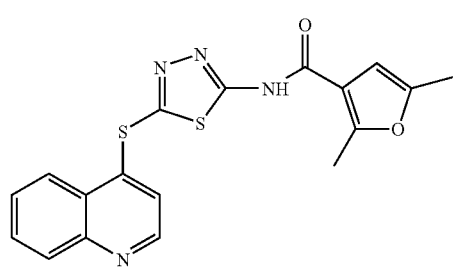
I-62
TABLE 1-continued
Examples of Compounds of Formula I:
I-63
I-64
I-65
I-66
I-67
I-68

TABLE 1-continued
Examples of Compounds of Formula I:
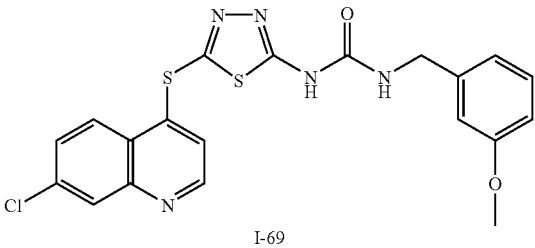
I-69
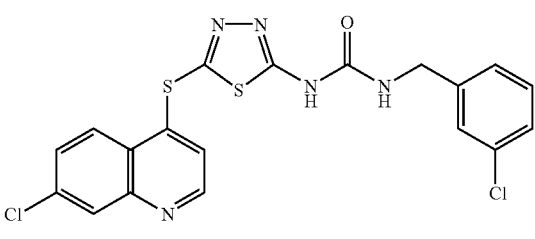
I-70
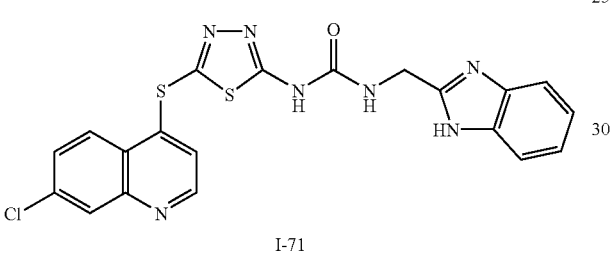
I-71
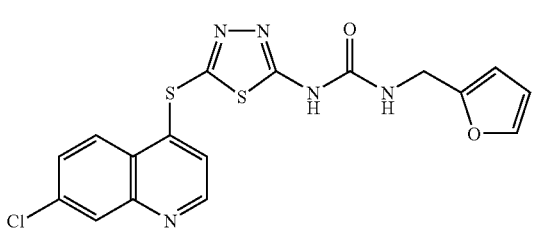
I-72
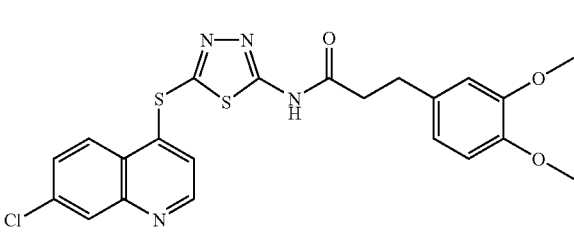
I-73
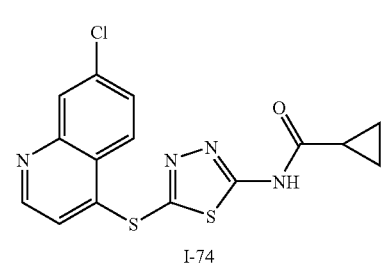
I-74
TABLE 1-continued
Examples of Compounds of Formula I:
I-75
I-76
I-77
I-78

TABLE 1-continued
Examples of Compounds of Formula I:
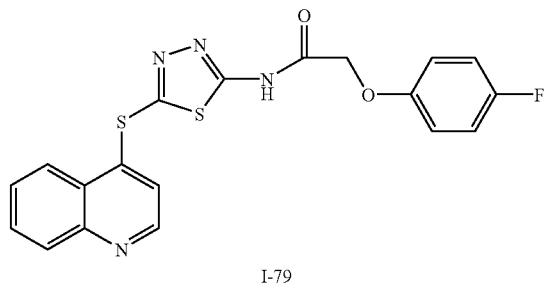
I-79
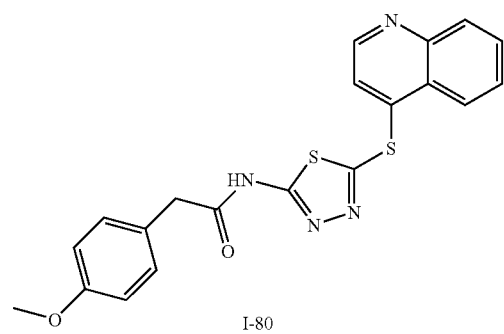
I-80
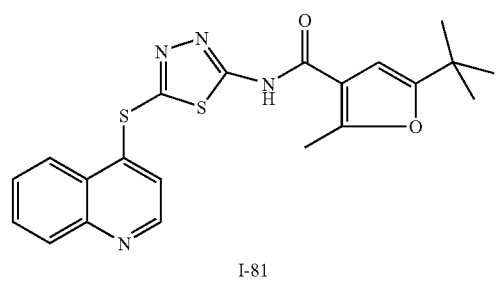
I-81
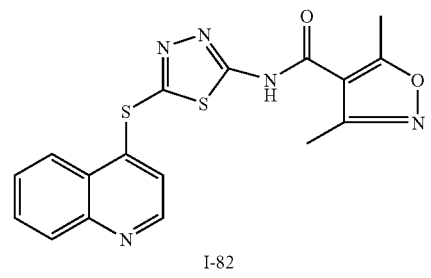
I-82
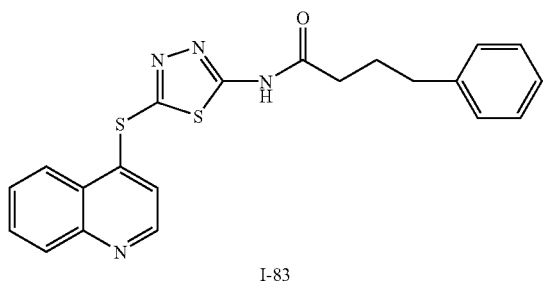
I-83
TABLE 1-continued
Examples of Compounds of Formula I:
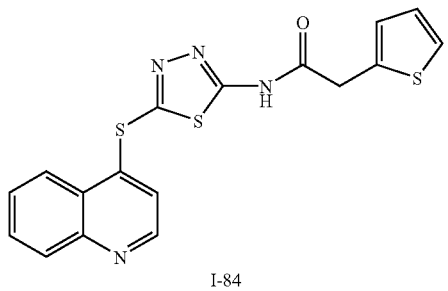
I-84
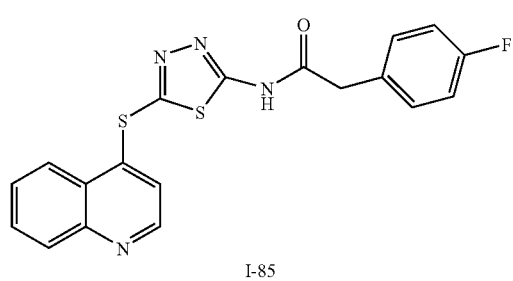
I-85
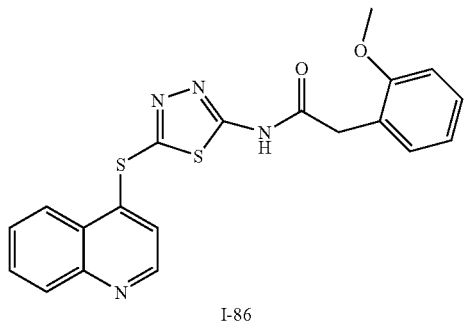
I-86
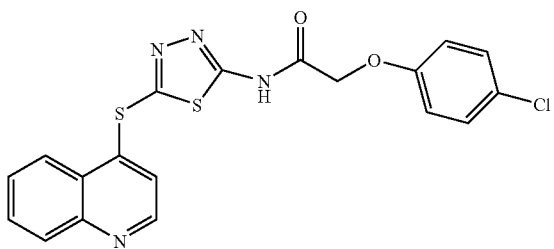
I-87
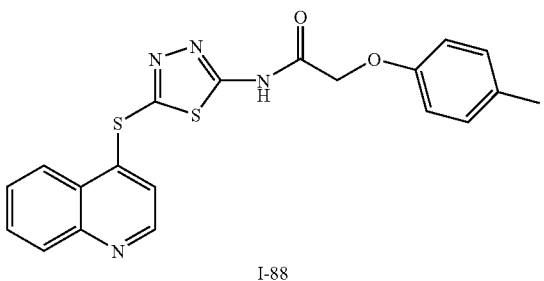
I-88

TABLE 1-continued
Examples of Compounds of Formula I:
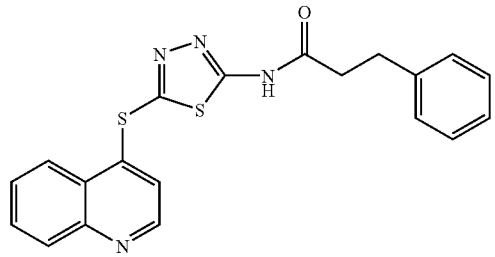
I-89
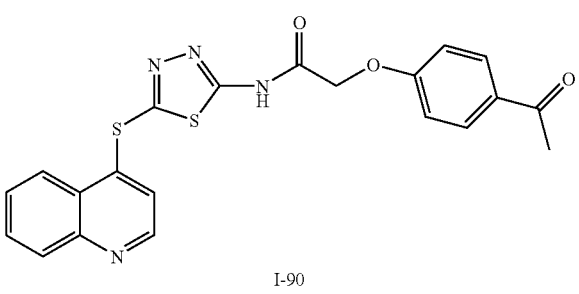
I-90
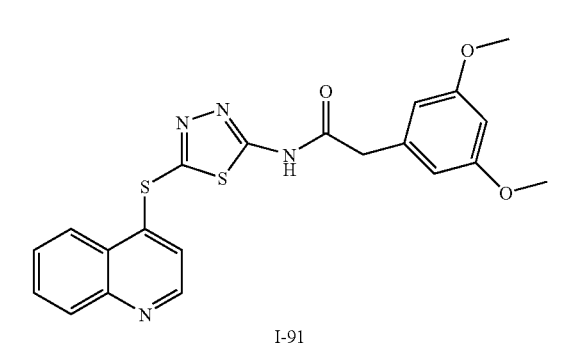
I-91
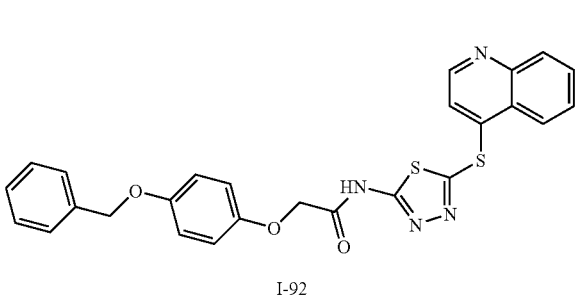
I-92
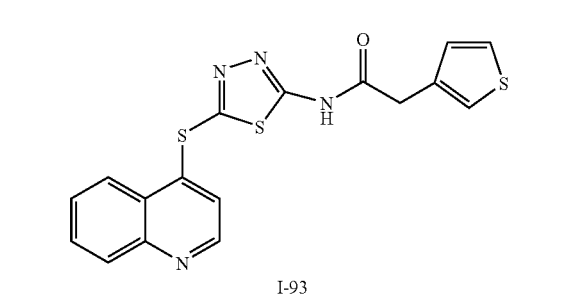
I-93
TABLE 1-continued
Examples of Compounds of Formula I:
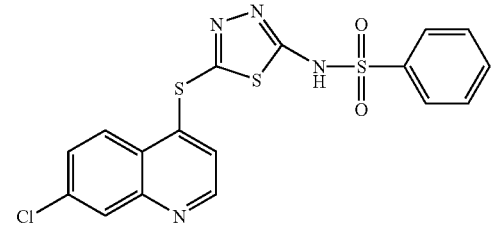
I-94
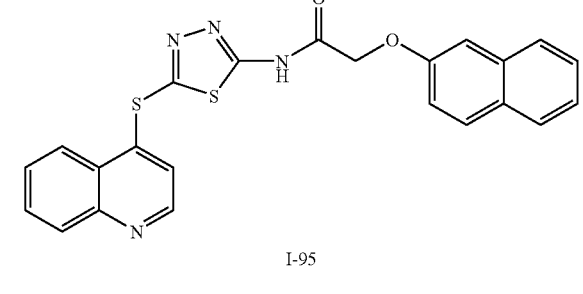
I-95
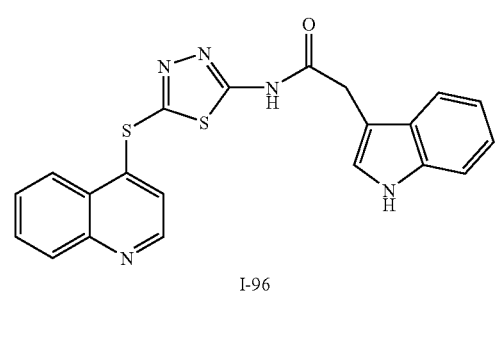
I-96
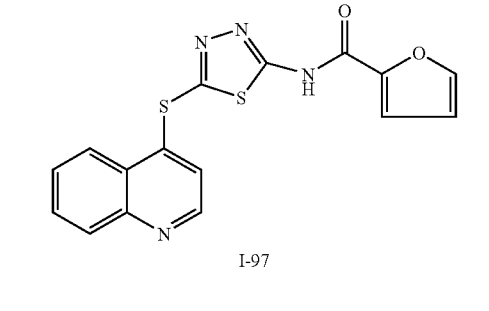
I-97
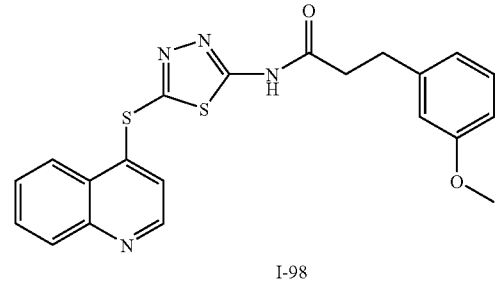
I-98

TABLE 1-continued
Examples of Compounds of Formula I:
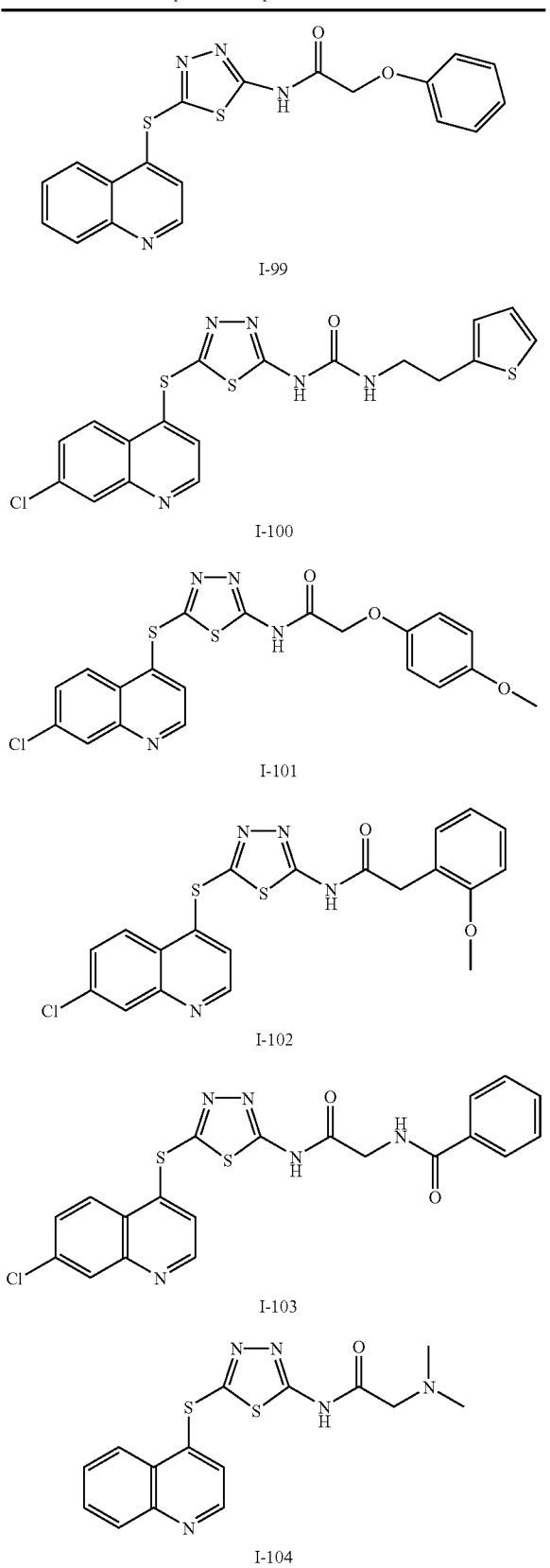
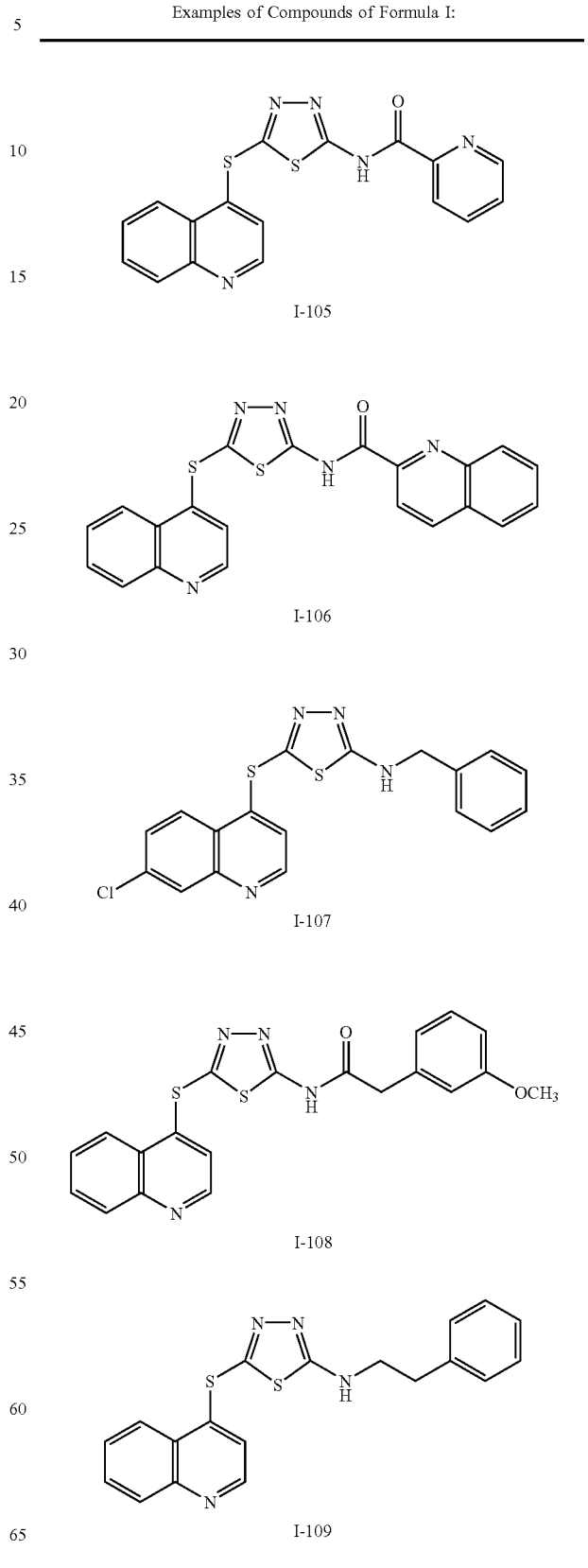

TABLE 1-continued

Examples of Compounds of Formula I:

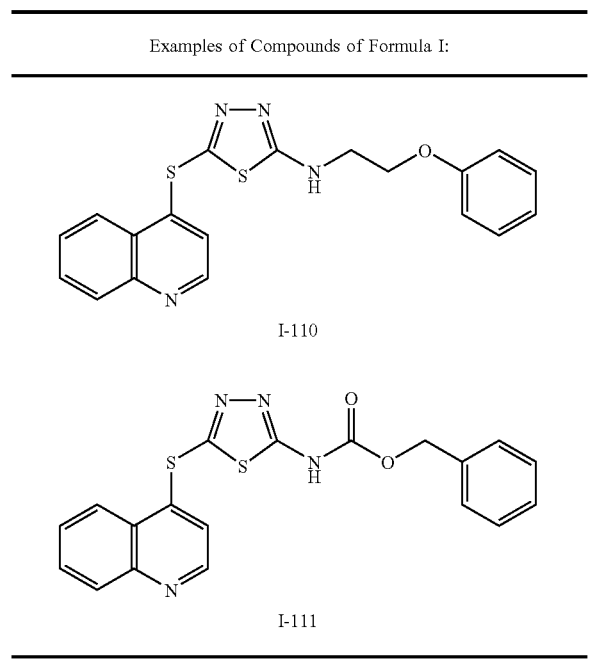

I-110

I-111

4. General Synthetic Methodology:

The compounds of this invention may be prepared in general by methods known to those skilled in the art for analogous compounds, as illustrated by the general scheme below, and the preparative examples that follow.

Scheme I

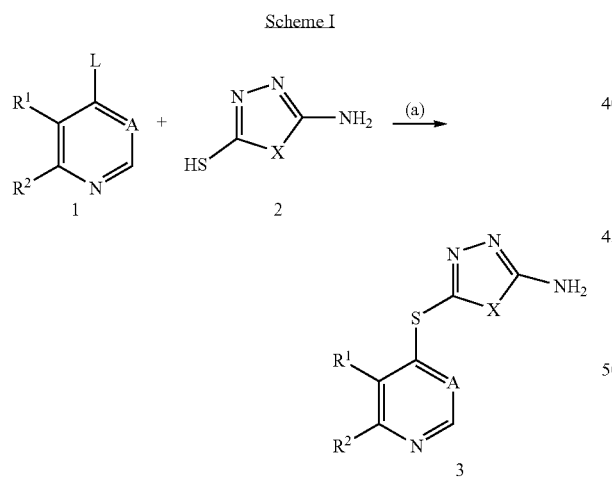

Reagents and conditions: (a) NaH, DMF

Scheme I above shows a general method for preparing compounds of formula I where Q is a valence bond and $R^3$ is hydrogen (3). The leaving group L of compound 1 may be displaced by the sulfide compound 2 to form compound 3. A variety of L leaving groups are useful for this synthesis, including but not limited to chloro and bromo. Compound 3 is a useful intermediate in forming a variety of compounds of formula I using methods known to one of skill in the art and as illustrated in the Synthetic Schemes below.

Scheme II

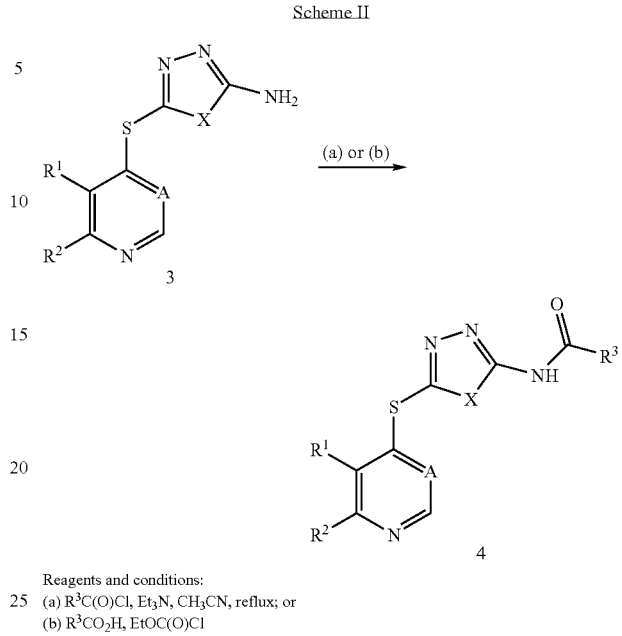

Reagents and conditions:
(a) $R^3C(O)Cl$, $Et_3N$, $CH_3CN$, reflux; or
(b) $R^3CO_2H$, $EtOC(O)Cl$ Scheme II above shows a method for preparing compounds of formula I wherein Q is a carbonyl group. These compounds may be prepared by treating compound 3 with an acid chloride of the formula $R^3C(O)Cl$ to form the amide compound 4. Alternatively, one may treat compound 3 with a carboxylic acid in the presence of a chloroformate as shown in step (b) above to form the amide compound 4. A wide variety of aliphatic and aryl acid chloride reagents are amenable to this reaction to form a variety of compounds of formula I wherein $R^3$ is aliphatic, aryl, heterocyclyl, or heteroaryl.

Scheme III

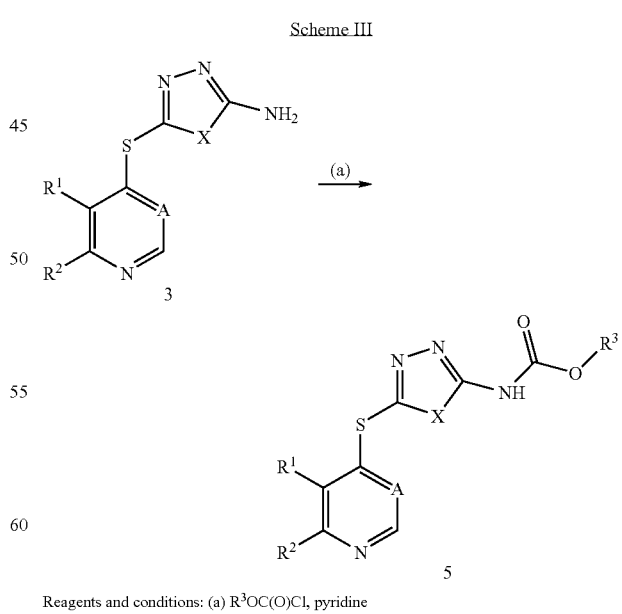

Reagents and conditions: (a) $R^3OC(O)Cl$, pyridine

Scheme III above shows a method for preparing compounds of formula I wherein Q is a $—CO_2—$ group. These compounds may be prepared by treating compound 3 with a chloroformate compound of formula R³OC(O)Cl to form the carbamate compound 5. A wide variety of aliphatic and aryl chloroformate reagents are amenable to this reaction to form a variety of compounds of formula I wherein R³ is aliphatic, aryl, heterocyclyl, or heteroaryl.

Scheme IV

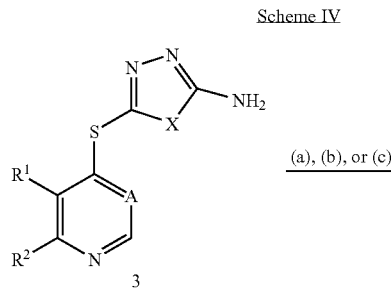

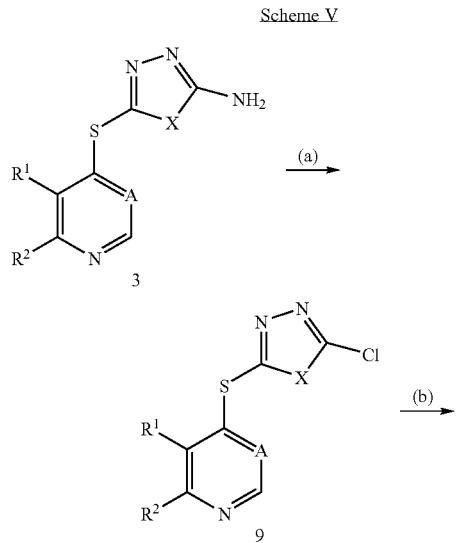

Reagents and conditions:
a) R³NCO, CH₃CN, reflux;
b) PhOCOCl, pyridine;
c) R³NH₂, DME, heat.

Scheme IV above shows a method for preparing compounds of formula I wherein Q is a —C(O)NH— group. These compounds may be prepared by treating compound 3 with an isocyanate compound of formula R³NCO to form the urea compound 6. A wide variety of aliphatic and aryl isocyanate reagents are amenable to this reaction to form a variety of compounds of formula I wherein R³ is aliphatic, aryl, heterocyclyl, or heteroaryl.

Scheme V

-continued

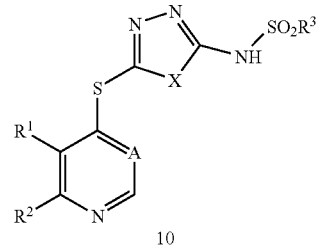

Reagents and conditions:
a) NaNO₂, HCl—H₂O;
b) R³SO₂NH₂, K₂CO₃

Scheme V above shows a general method for preparing compounds of formula I wherein Q is —SO₂—. Compound 3 may be treated with sodium nitrate in the presence of HCl—H₂O to form the chloro compound 9. The chloro substituent of compound 9 may then be displaced by a reagent having the formula R³SO₂NH₂ in order to form the sulfonamide compound 10. A wide variety of aliphatic and aryl sulfonamide reagents are amenable to this reaction to form a variety of compounds of formula I wherein R³ is aliphatic, aryl, heterocyclyl, or heteroaryl.

Scheme VI

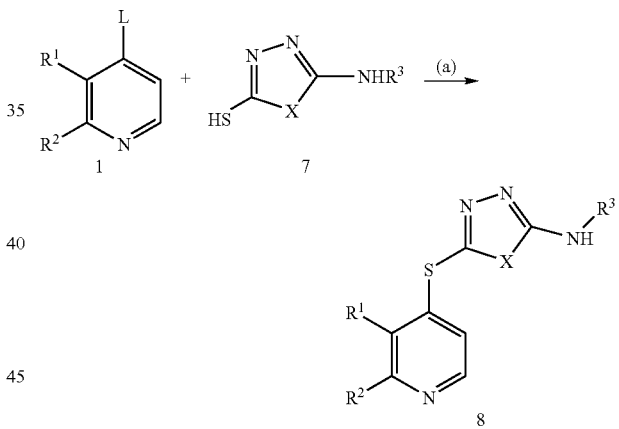

Reagents and conditions: a) NaH, DMF

Scheme VI above shows an alternative method for preparing compounds of the present invention wherein Q is a valence bond (8). The leaving group L of compound 1 may be displaced by the sulfide compound 7 to form compound 8. A variety of L leaving groups are useful for this synthesis, including but not limited to chloro and bromo. A wide variety of aliphatic and aryl sulfonamide reagents are amenable to this reaction to form a variety of compounds of formula I wherein R³ is aliphatic, aryl, heterocyclyl, or heteroaryl.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration
Pharmaceutically Acceptable Compositions As discussed above, the present invention provides compounds that are inhibitors of protein kinases, and thus the present compounds are useful for the treatment of diseases, disorders, and conditions including, but not limited to, allergic disorders such as asthma and atopic dermatitis, autoimmune diseases such as SLE lupus and psoriasis, and conditions associated with organ transplantation.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

Certain compounds of the present invention are commercially available (Maybridge plc, Trevillett, Tintagel, Cornwall PL34 OHW, England). However, these compounds are not known as inhibitors of JAK kinase nor as having any pharmaceutical use or as a component of a pharmaceutically acceptable composition. Commercially available compounds of the present invention are selected from:

3-Chloro-benzo[b]thiophene-2-carboxylic acid [5-(7-chloro-quinolin-4-ylsulfanyl)-[1,3,4]thiadiazol-2-yl]-amide;
N-[5-(7-Chloro-quinolin-4-ylsulfanyl)-[1,3,4]thiadiazol-2-yl]-2-phenoxy-nicotinamide;
5-Methyl-2-phenyl-2H-[1,2,3]triazole-4-carboxylic acid [5-(7-chloro-quinolin-4-ylsulfanyl)-[1,3,4]thiadiazol-2-yl]-amide;
Cyclopropanecarboxylic acid [5-(7-chloro-quinolin-4-ylsulfanyl)-[1,3,4]thiadiazol-2-yl]-amide;
N-[5-(7-Chloro-quinolin-4-ylsulfanyl)-[1,3,4]thiadiazol-2-yl]-acetamide;
Thiophene-2-carboxylic acid [5-(7-chloro-quinolin-4-ylsulfanyl)-[1,3,4]thiadiazol-2-yl]-amide;
5-(6-Ethyl-thieno[2,3-d]pyrimidin-4-ylsulfanyl)-[1,3,4]thiadiazol-2-ylamine;
5-(2-Chloro-thieno[2,3-b]pyridin-4-ylsulfanyl)-[1,3,4]thiadiazol-2-ylamine;
2-Chloro-N-[5-(7-chloro-quinolin-4-ylsulfanyl)-[1,3,4]thiadiazol-2-yl]-2-methyl-propionamide;
2-Chloro-N-[5-(7-chloro-quinolin-4-ylsulfanyl)-[1,3,4]thiadiazol-2-yl]-2 -methyl-propionamide;
4-Hydroxy-2-oxo-2,3-dihydro-quinoline-3-carboxylic acid [5-(7-chloro-quinolin-4-ylsulfanyl)-[1,3,4]thiadiazol-2-yl]-amide;
1,3,4-thiadiazol-2-amine, 5-[(7-methylthieno [3,2-d] pyrimidin-4-yl)thio]-; and
Acetamide, N[5-(1H-purin-6-ylthio)-1,3,4-thiadiazol-2-yl.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a JAK-3 kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of allergic disorders such as asthma and atopic dermatitis, autoimmune diseases such as SLE lupus and psoriasis, and conditions associated with organ transplantation is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for the treatment of allergic disorders such as asthma and atopic dermatitis, autoimmune diseases such as SLE lupus and psoriasis, and conditions associated with organ transplantation.

The compounds and compositions, according to the method of the present invention, may be administered using any amount and any route of administration effective for treating or lessening the severity of allergic disorders such as asthma and atopic dermatitis, autoimmune diseases such as SLE lupus and psoriasis, and conditions associated with organ transplantation.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of JAK-3, and thus, without wishing to be bound by any particular theory, the compounds and compositions are particularly useful for treating or lessening the severity of a disease, condition, or disorder where activation of one or more of JAK-3 is implicated in the disease, condition, or disorder. When activation of JAK-3 is implicated in a particular disease, condition, or disorder, the disease, condition, or disorder may also be referred to as "JAK-3-mediated disease" or disease symptom. Accordingly, in another aspect, the present invention provides a method for treating or lessening the severity of a disease, condition, or disorder where activation or one or more of JAK-3 is implicated in the disease state.

The activity of a compound utilized in this invention as an inhibitor of JAK-3, may be assayed in vitro, in vivo or in a cell line. In vitro assays include assays that determine inhibition of either the phosphorylation activity or ATPase activity of activated JAK-3. Alternate in vitro assays quantitate the ability of the inhibitor to bind to JAK-3. Inhibitor binding may be measured by radiolabelling the inhibitor prior to binding, isolating the inhibitor/JAK-3, complex and determining the amount of radiolabel bound. Alternatively, inhibitor binding may be determined by running a competition experiment where new inhibitors are incubated with JAK-3 bound to known radioligands.

The term "measurably inhibit", as used herein means a measurable change in JAK-3 activity between a sample comprising said composition and a JAK-3 kinase and an equivalent sample comprising JAK-3 kinase in the absence of said composition.

The term "JAK-mediated disease", as used herein means any disease or other deleterious condition in which a JAK family kinase, in particular JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting JAK-3 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JAK-3 kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

A) General $^1$H NMR spectra were recorded at 400 MHz using a Bruker DPX 400 instrument. $^{13}$C NMR spectra were recorded at 100 MHz using the same instrument. LC/MS data were obtained using a Micromass ZQ or platform instrument with atmospheric pressure chemical ionisation. HPLC analysis were performed on a Phenomenex $C_{18(2)}$ Luna column (30×4.6 mm) maintained at 40° C. Samples were prepared as solutions in acetonitrile with approximate concentration of 1 mg/mL. 1-5 μL were injected into the system. The compound was eluted using the following gradient at a flow rate of 2 mL/min:

0 min, 80% $H_2O$-20% MeCN, 2.5 min, 0% $H_2O$-100% MeCN, 3.5 min, 0% $H_2O$-100% MeCN The eluent mixture was then returned to the starting conditions and the column re-equilibrated for 1 min. Detection was via a diode array detector, the chromatograms for 214 and 254 being extracted. In all cases the elution time was identical for the two wavelengths.

All reagents were obtained commercially and used directly. DMF was dried over 4 Å molecular sieves (Fisher Scientific). Column chromatography employed Silica Gel 60 (Fluka). TLC was carried out using pre-coated plastic sheets Polygram SIL G/UV$_{254}$ (Macherey-Nagel).

B) Synthesis of Exemplary Compounds:

In general, as depicted in the examples below,

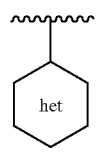

represents

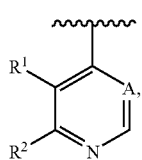

represents

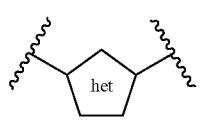

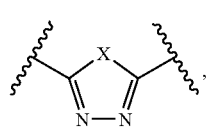

and R (as used in the general schemes below) represents $R^3$ as defined generally and in subsets herein. It will be appreciated that the rings described above may be substituted as generally described and exemplified herein.

General Procedure for the Condensation of 5-amino-[1,3,5]thiadiazole-2-thiole and Chloroheterocyclic Compound

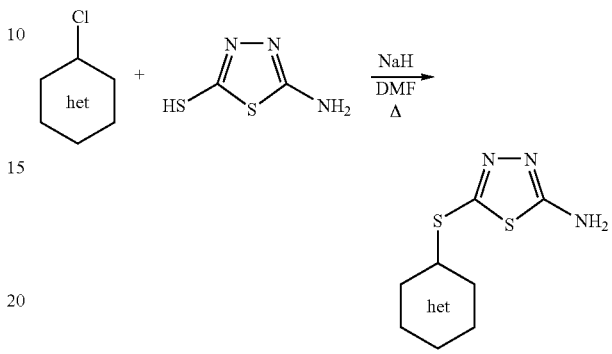

NaH (1.2 mmol) was added in portions to a solution of 5-amino-thiadiazole-2-thiol (1.1 mmol) in DMF (8 ml) at room temperature. After the addition was completed, the mixture was stirred at room temperature for 20 min. The chloroheterocyclic compound (1.1 mmol) was then added in one portion and the mixture heated at 80-90° C. (oil bath temperature) for 18 h. The reaction mixture was allowed to cool to room temperature and water (20-40 ml) was added. The precipitate was separated by filtration, washed several times with cold water, then with Et$_2$O and dried to afford the product (25-96% yield).

General Procedure for the Preparation of Amides

Procedure A:

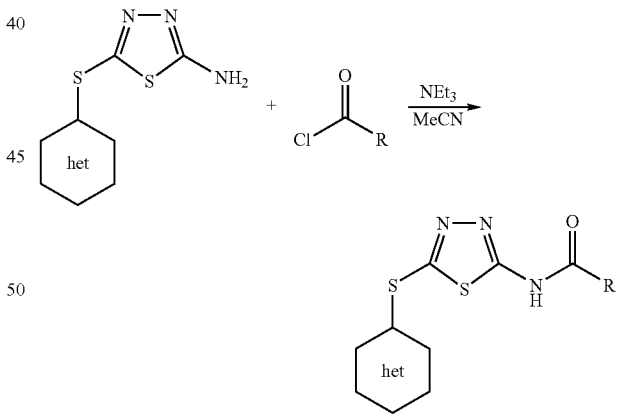

NEt$_3$ (0.45 mmol) was added dropwise to a suspension of the amine (0.3 mmol) in MeCN (9 ml). The mixture was then cooled to 0° C. and the acid chloride (0.36 mmol) was added dropwise. After being stirred at 0° C. for 20 min, the mixture was allowed to warm to room temperature and then heated at 80° C. (oil bath temperature) for 18 h. The product crystallised during the reaction and was separated by filtration from the warm solution, washed with cold Et$_2$O and dried. In cases where the product did not crystallize, the solvent was evaporated under reduced pressure and the solid residue suspended in water (~5 ml). Undissolved material was separated by filtration, washed several times with water, then with Et$_2$O and dried to afford the product (40-96% yield).

Procedure B

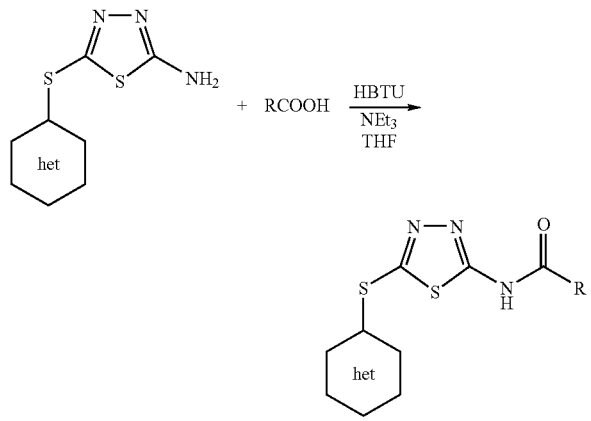

To a suspension of amine (0.34 mmol) in THF (15 ml), acid (0.37 mmol) was added followed by NEt$_3$ (0.41 mmol). The mixture was then cooled to 0° C. and HBTU (0.37 mmol) was added in one portion. After being stirred for 40 min at 0° C., the mixture was warmed to room temperature and then heated at 50-60° C. (oil bath temperature) for 18 h. The reaction mixture was allowed to cool to room temperature and water (~40 ml) was added. The precipitate was separated by filtration, washed several times with water, Et$_2$O and then dried to afford the product (43-56% yield).

Procedure C

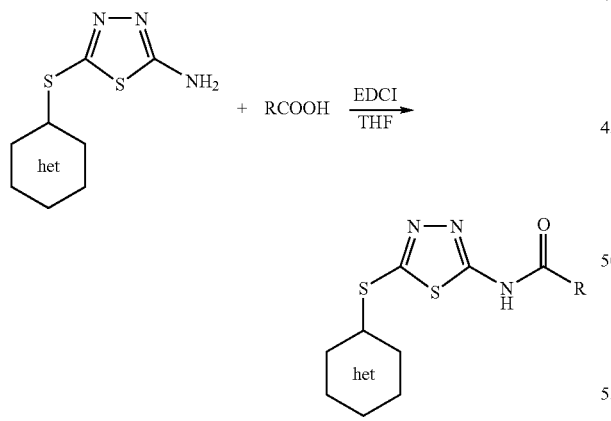

To a suspension of acid (0.39 mmol) in THF (15 ml), amine was added (0.43 mmol) followed by EDCI (0.78 mmol). The mixture was heated at 60° C. under nitrogen atmosphere for 18 h. The reaction mixture was allowed to cool to room temperature and water (~40 ml) was added. The precipitate was separated by filtration washed with a small amount of water, Et$_2$O and dried to afford the product (58-69% yield).

Purification of Amides

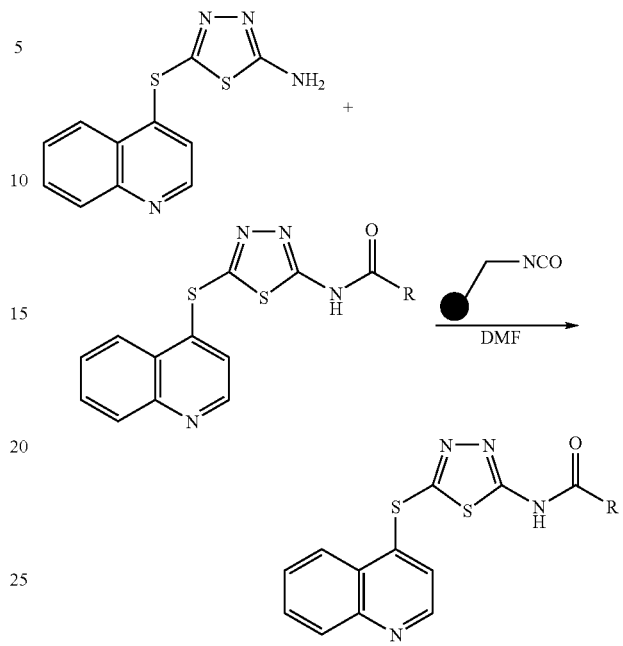

When the product is a mixture of the amide and the starting amine the following procedure was used for the further purification:

The mixture (0.15 mmol), (including ~15% amine, based on $^1$H NMR), was dissolved in DMF (2 ml). To this solution, methylisocyanate polystyrene (3 eq) was added and the mixture was shaken at 50-60° C. for 18 h. After being cooled to room temperature, the mixture was filtered and the resin washed with warm DMF (3×~2 ml). The solvent was evaporated under reduced pressure, and the solid residue was washed with Et$_2$O and dried to afford the product.

General Procedure for the Preparation of Carbamate Derivatives

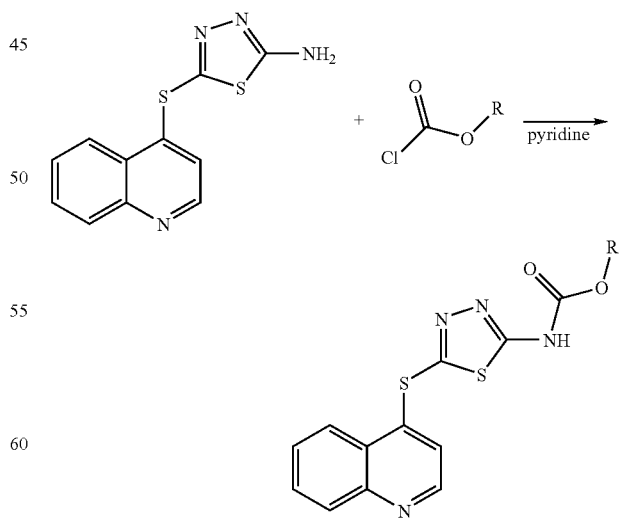

The chlorocarbamate (0.33 mmol) was added dropwise to a mixture of the amine (0.26 mmol) in dry pyridine cooled to 0° C. The mixture was allowed to warm to room temperature and stirred for an additional 48 h. Water (5 ml) was then added, the precipitate collected by filtration, washed with water and Et₂O and dried to afford the product (41-72% yield).

When the starting amine is present in the product, the product was purified by the method described above using methylisocyanate polystyrene.

General Procedures for the Preparation of Urea Derivatives

Procedure A

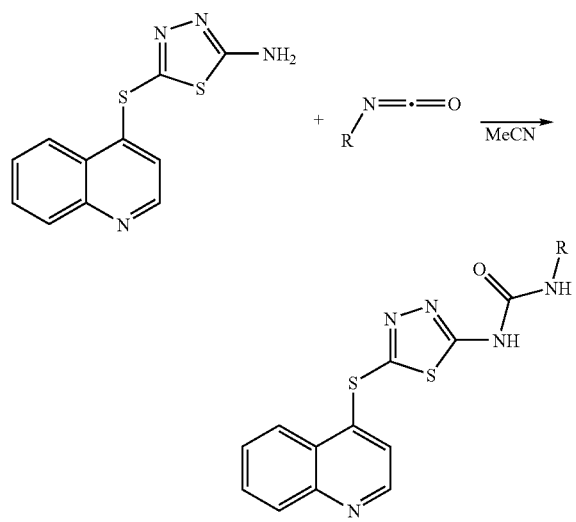

Isocyanate (0.29 mmol) was added to a suspension of amine (0.22 mmol) in MeCN (10 ml) and the mixture was heated at 70-75° C. (oil bath temperature) for 18 h. The product precipitated during the reaction and was separated from the warm reaction mixture by filtration, washed with Et₂O and dried (35-67% yield).

Procedure B

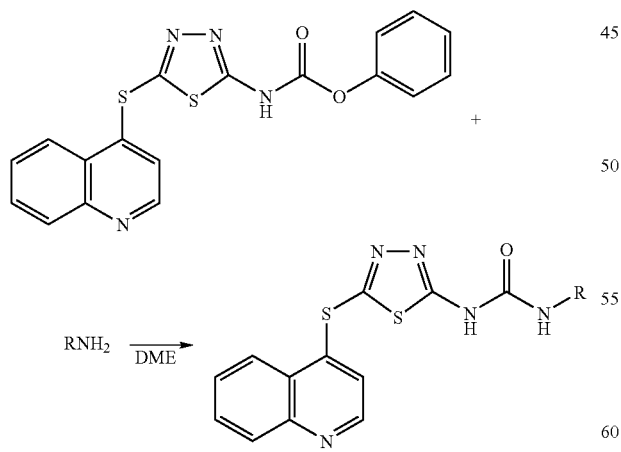

Amine (0.19 mmol) was added to a suspension of carbamate (0.15 mmol) in DME (10 ml) and the mixture was then heated at ~80° C. (oil bath temperature) for 18 h. The solvent was evaporated and the solid residue washed with Et₂O several times to afford the product (14-63% yield).

Synthesis of 4-(5-chloro-[1,3,4]thiadiazol-2-yl sulfanyl) quinoline

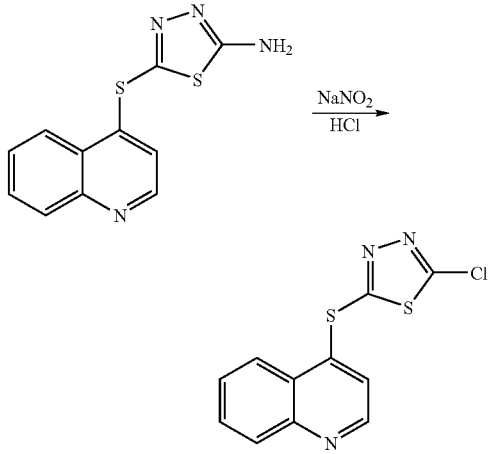

To a solution of amine (4.93 mmol) in conc. HCl (20 ml) cooled to −10° C., NaNO₂ (14.8 mmol) dissolved in H₂O (4 ml) was added dropwise, keeping temperature below 0° C. The reaction mixture was stirred at the same temperature for an additional 3 h and then allowed to warm to room temperature. H₂O (20 ml) was added, the mixture neutralised with solid K₂CO₃ and extracted (EtOAc). The extract was dried (MgSO₄), the solvent evaporated under reduced pressure and the residue purified by column chromatography (SiO₂, petroleum ether/ethyl acetate, 1:1 v/v) to afford the product (53-95% yield).

General Procedure for the Preparation of 4-(5-amino-[1,3,4]thiadiazol-2-yl sulfanyl)quinoline Derivatives

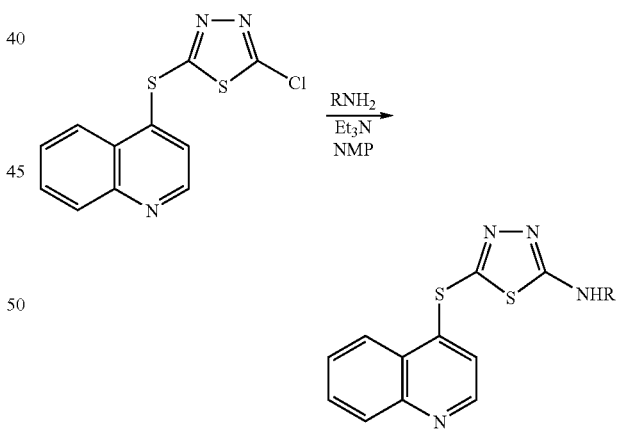

To a solution of chloride (0.72 mmol) in NMP (5 ml), NEt₃ (0.8 mmol) was added followed by amine (0.72 mmol). The mixture was heated at 70° C. (stem block temperature) under nitrogen atmosphere for 72 h. The solvent was then evaporated under reduced pressure and the residue partitioned between EtOAc/H₂O (20 ml, 1:1 v/v). The organic layer was separated and the water layer extracted (EtOAc). The combined organic layers were dried (MgSO₄), the solvent evaporated under reduced pressure and the residue purified by column chromatography (SiO₂, petroleum ether/EtOAc 1:1 v/v) to afford the product.

General Procedure for the Preparation of Sulfonamide Derivatives

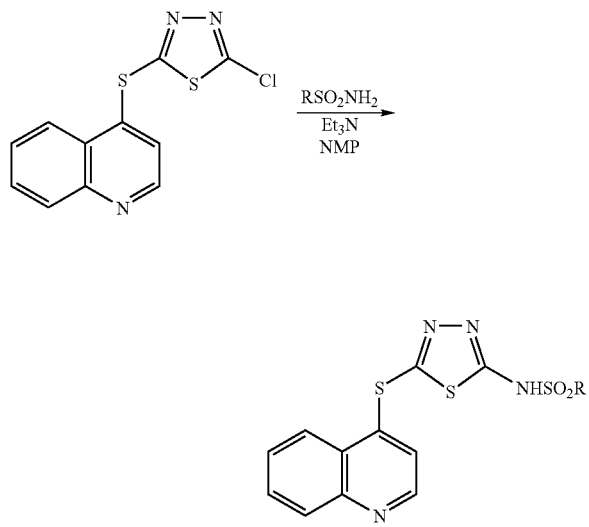

To a solution of chloride (0.12 mmol) in DMF (2 ml), sulfonamide (0.14 mmol) was added followed by $K_2CO_3$ (0.24 mmol) and the mixture was heated at 70° C. (oil bath temperature) for 72 h. The solvent was evaporated under reduced pressure and the residue partitioned between EtOAc/$H_2O$ (20 ml, 1:1 v/v). The water layer was separated, acidified (2M HCl) to pH 2 and then extracted (EtOAc). The extract was dried ($MgSO_4$) and the solvent evaporated under reduced pressure to afford the product (8-56% yield).

General Procedure for the Condensation of N-Substituted 5-amino-thiadiazole-2-thiole and 4,7-dichloro-quinoline

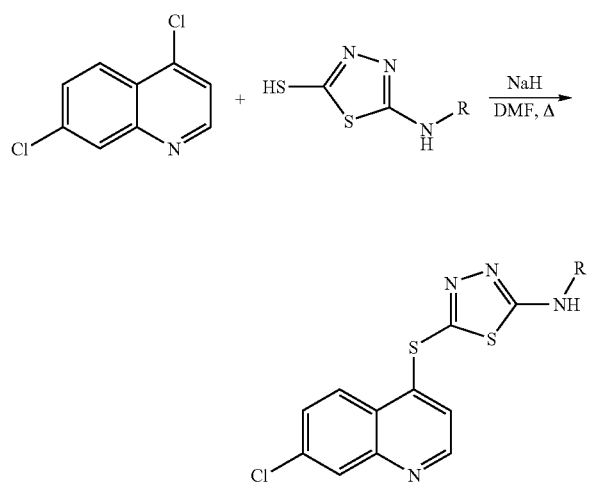

NaH (1.2 mmol) was added in portions to a solution of N-subtituted 5-amino-thiadiazole-2-thiole (1.1 mmol) in DMF (8 ml) at room temperature under nitrogen atmosphere and the mixture was then stirred for 20 min. Chloroheterocyclic compound (1.1 mmol) was then added in one portion and the mixture heated at 70° C. (oil bath temperature) for 3-18 h. The reaction mixture was allowed to cool to room temperature and water (20-40 ml) was added. The precipitated product was separated by filtration, washed several times with cold water and then with $Et_2O$ and dried to afford the product (10-95% yield).

Synthesis of 5-(7-Chloro-quinolin-4-yloxy)-[1,3,4]thiadiazole-2-carboxylic Acid Ethyl Ester

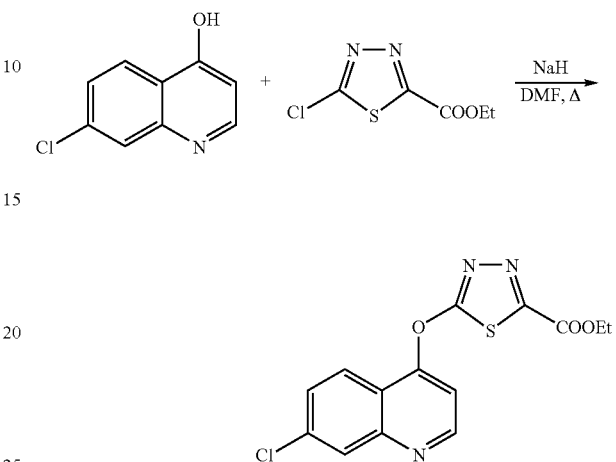

NaH (0.022 mg, 0.5 mmol) was added in portions to a solution of 7-chloro-4-hydroxyquinoline (0.093 mg, 0.5 mmol) in DMF (6 ml) at room temperature and the mixture stirred at room temperature for 20 min. 2-Chloro-[1,3,4]thiadiazole derivative (0.097 mg, 0.5 mmol) was then added in one portion and the mixture heated at 70-80° C. (oil bath temperature) for 18 h. The reaction mixture was allowed to cool to room temperature and water (15-30 ml) was added. The precipitate was separated by filtration, washed several times with cold water, then with $Et_2O$ and dried to afford the product (0.081 mg, 47% yield).

Synthesis of (7-Chloro-quinolin-4-yloxy)-[1,3,4]thiadiazole-2-carboxylic Acid (Furan-2-ylmethyl)-amide

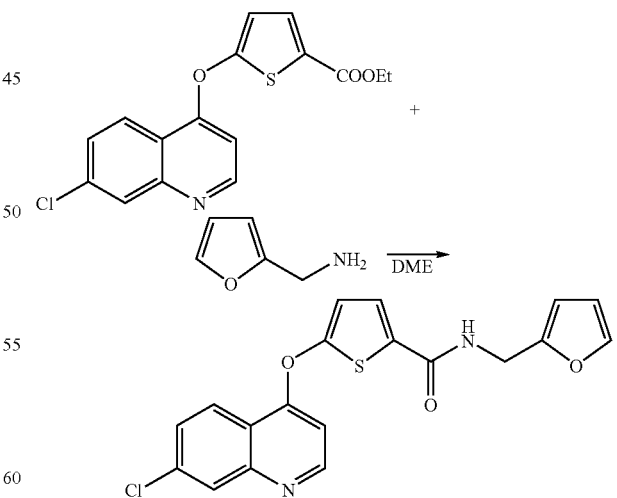

Ester (0.042 mg, 12.0 mmol) was added to a solution of the amine (0.035 mg, 0.36 mmol) in DME (4 ml). The mixture was heated at 80° C. for 18 h. The solvent was evaporated and the residue triturated with $Et_2O$ to afford the product (0.035 mg, 75%).

General Procedure for the Condensation of Heterocyclic Thiols and Heterocyclic Bromides

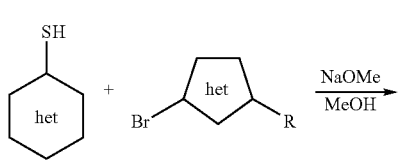

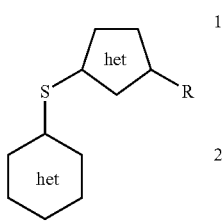

R = NO$_2$, NH$_2$

NaOMe (19.2 mmol) was added in portions to a suspension of the bromo derivative (16 mmol) and the thiol (16 mmol) in MeOH (15 ml) under nitrogen atmosphere at 0° C. The mixture was stirred at 0° C. for 10 min, warm to room temperature and then heated at 45-50° C. for 4-18 h. Reaction mixture was allowed to cool to room temperature, the solvent evaporated under reduced pressure and the residue purified by column chromatography (SiO$_2$, Et$_2$O) to afford the product.

Synthesis of Heterocyclic Amines from Heterocyclic Nitro Compounds

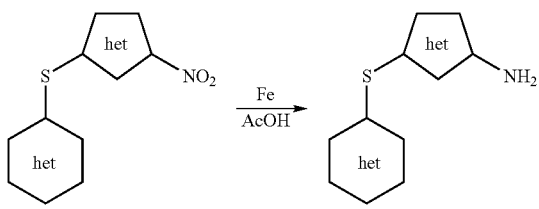

Activated Fe (0.22 g, 3.9 mmol) was added to a solution of the 2-nitrothiophene derivative (0.1 g, 0.3 mmol) in AcOH (3 ml). The mixture was heated at 80° C. (oil bath temperature) for 10 min, allowed to cool to room temperature and then filtered over celite. The celite cake was washed with H$_2$O. The filtrate was extracted (EtOAc), the aqueous layer was basified (Na$_2$CO$_3$) and extracted (EtOAc). The combined organic layers were washed with NaOH solution (2M), dried (Mg$_2$SO$_4$) and the solvent removed under reduced pressure. The residue was purified by column chromatography (SiO$_2$, Et$_2$O) to afford the product.

Synthesis of Thiophene-2-carboxylic Acid Amides

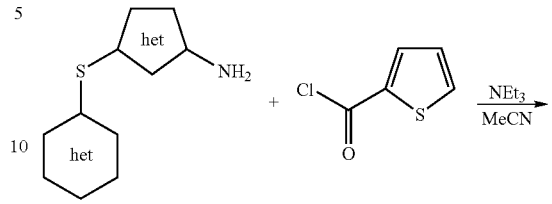

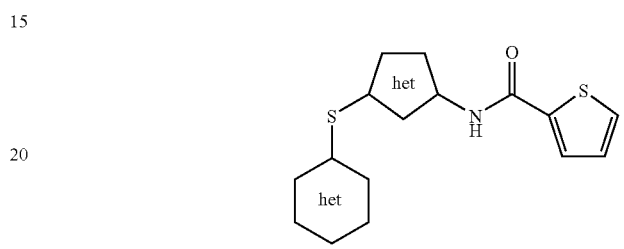

These compounds have been made according to the general procedure (procedure A) for the preparation of amides. The crude reaction mixture was purified by column chromatography (SiO$_2$, Et$_2$O) to afford the product (18-62% yield).

Synthesis of 5-Chloro-[1,3,4]thiadiazole-2-carboxylic Acid (7-chloro-quinolin-4-yl)-amide

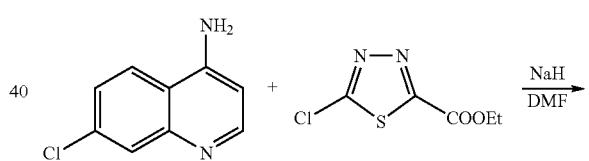

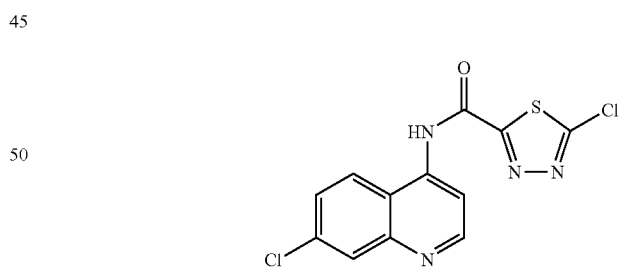

NaH (0.023 g, 0.58 mmol) was added in portions to a solution of 4-amino-7-chloro-quinoline (0.1 g, 0.56 mmol) in DMF (6 ml) at room temperature and the mixture was stirred for 20 min. 5-Chloro-[1,3,4]thiadiazole derivative (0.108 g, 0.56 mmol) was then added in one portion and the mixture heated at 80° C. (oil bath temperature) for 18 h. The reaction mixture was allowed to cool to room temperature and water (15 ml) was added. The precipitate was separated by filtration, washed with Et$_2$O and dried to afford the product (0.08 g, 60% yield).

LCMS data are presented in Table 2 below for exemplary compounds of the invention:
TABLE 2
| Structure | (M + H)+ |
| --- | --- |
| 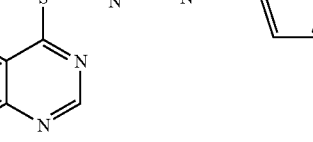 | 355 |
| 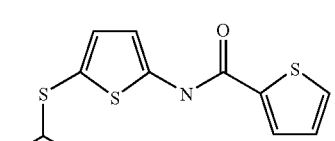 | 369 |
| 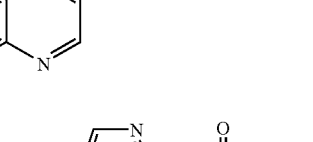 | 370 |
| 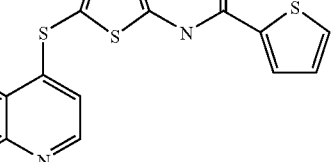 | 416 |
| 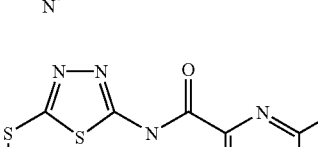 | 346 |
| 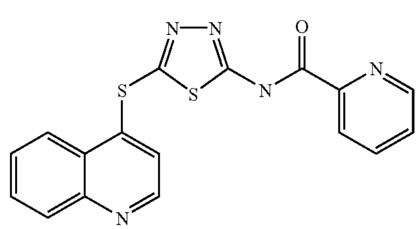 | 366 |

TABLE 2-continued
| Structure | (M + H)+ |
|---|---|
| 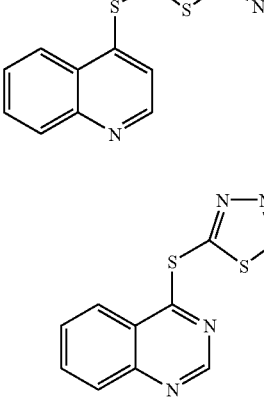 | 422 |
| 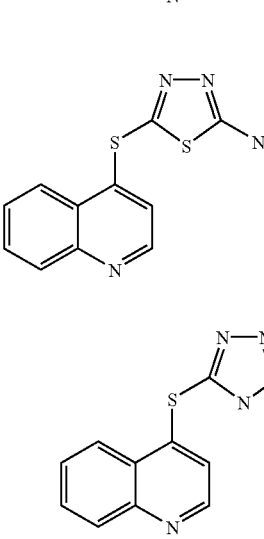 | 372 |
| 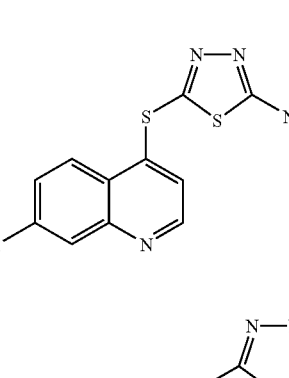 | 409 |
| 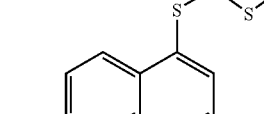 | 354 |
| 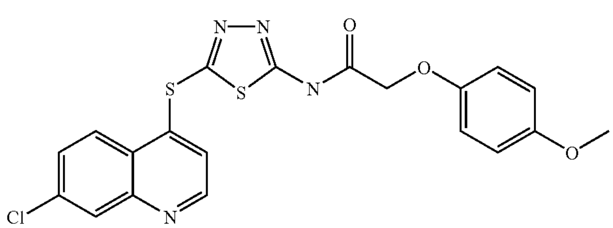 | 459 |
| 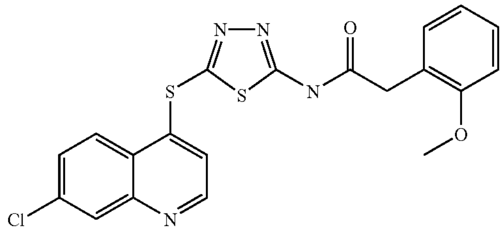 | 443 |

TABLE 2-continued

| Structure | (M + H)+ |
|---|---|
| 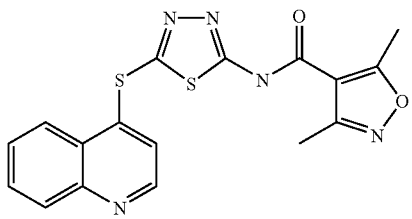 | 384 |
| 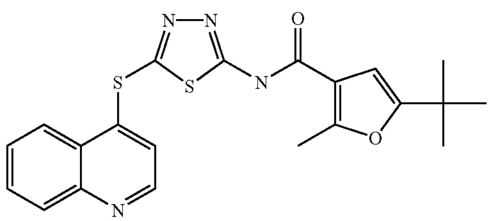 | 425 |
| 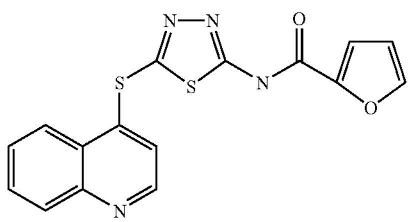 | 355 |
| 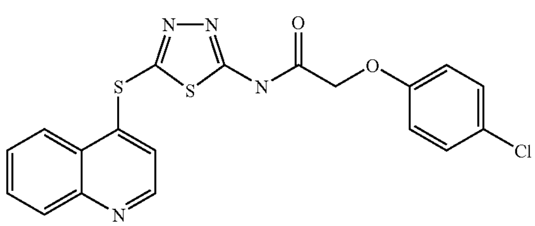 | 429 |
| 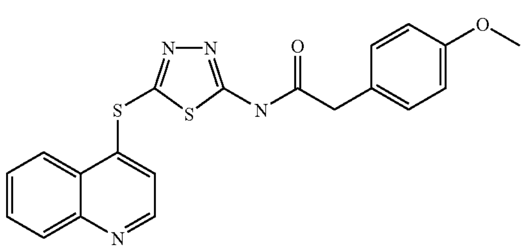 | 409 |
| 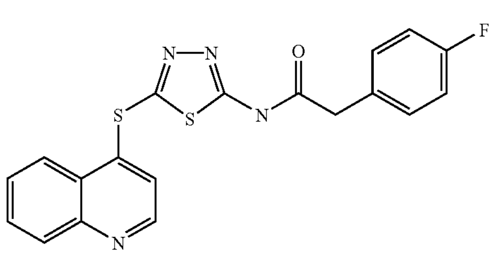 | 397 |

TABLE 2-continued

| Structure | (M + H)+ |
|---|---|
| 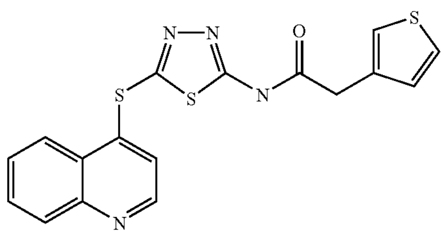 | 385 |
| 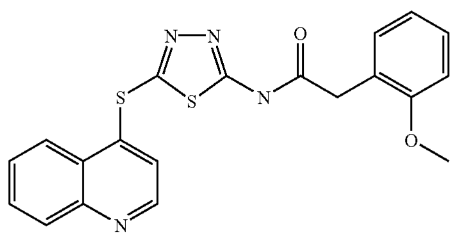 | 409 |
| | 439 |
| | 439 |
| 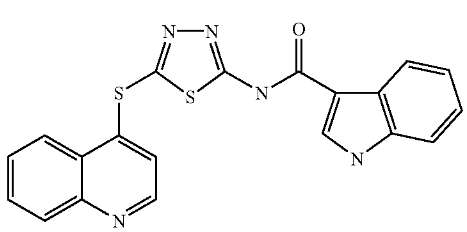 | 404 |
| 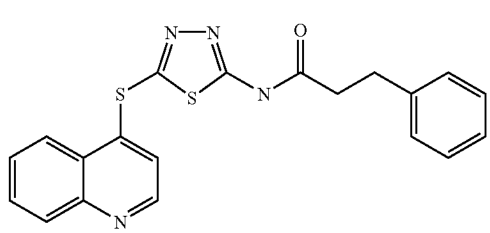 | 393 |

TABLE 2-continued

| Structure | (M + H)+ |
|---|---|
| 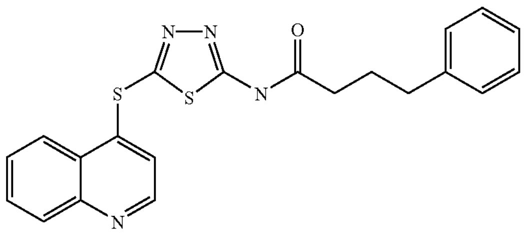 | 407 |
| 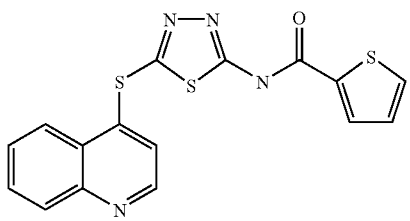 | 371 |
| 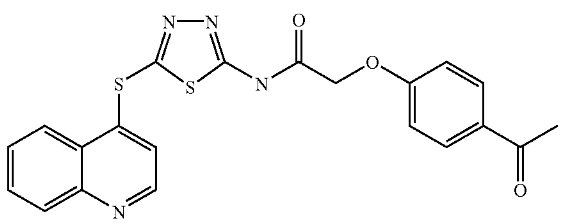 | 437 |
| 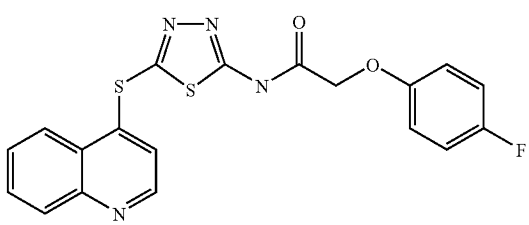 | 413 |
| 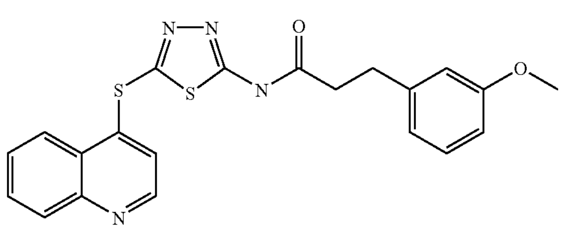 | 423 |
| 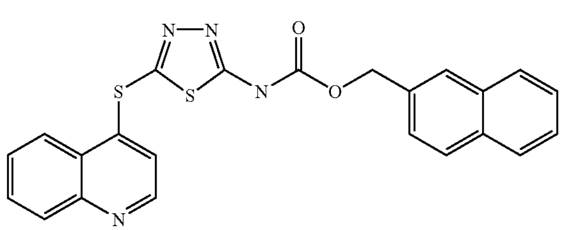 | 445 |

TABLE 2-continued
| Structure | (M + H)+ |
|---|---|
| 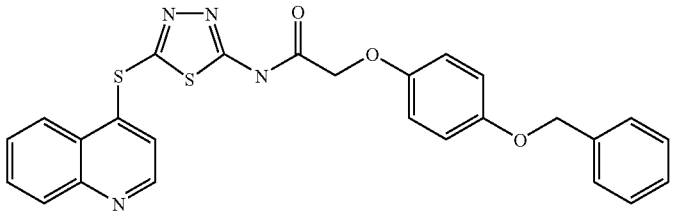 | 501 |
| 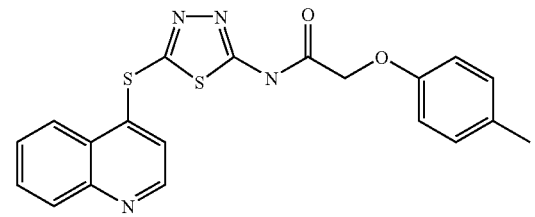 | 409 |
| 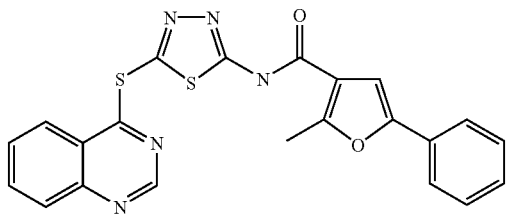 | 446 |
| 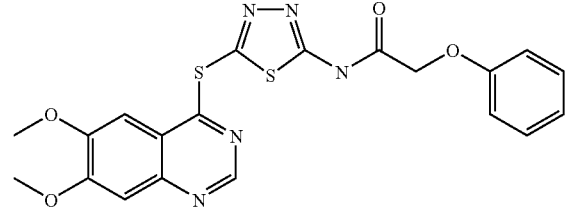 | 456 |
| 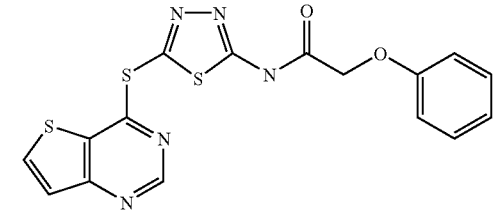 | 402 |
| 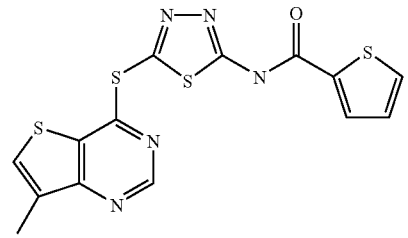 | 392 |

TABLE 2-continued

| Structure | (M + H)+ |
|---|---|
| 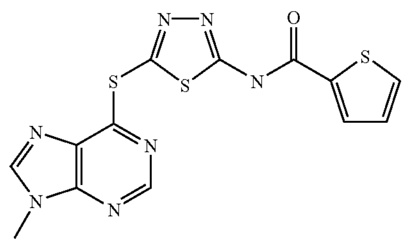 | 376 |
| 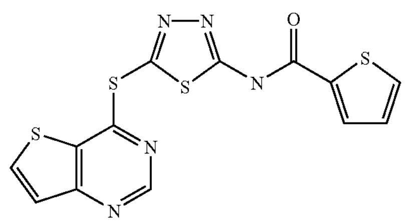 | 378 |
| 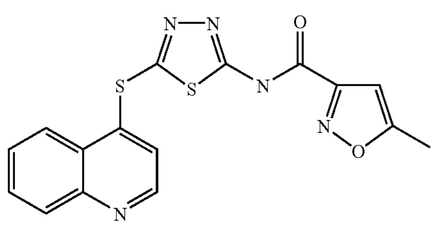 | 370 |
| 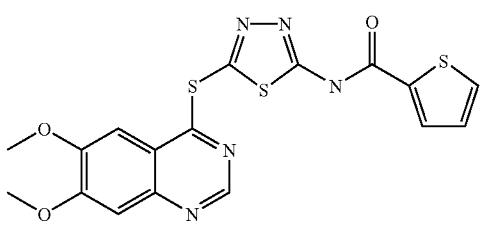 | 432 |
| 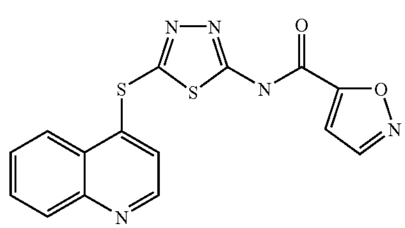 | 356 |
| 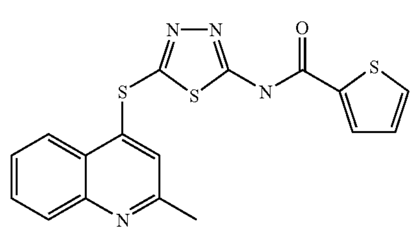 | 385 |

TABLE 2-continued

| Structure | (M + H)+ |
|---|---|
| | 405 |
| 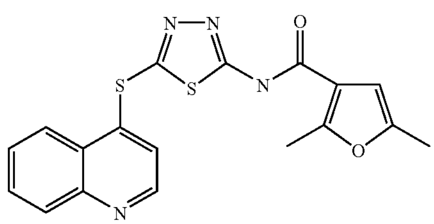 | 383 |
| 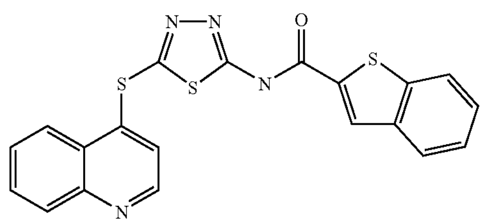 | 421 |
| | 405 |
| 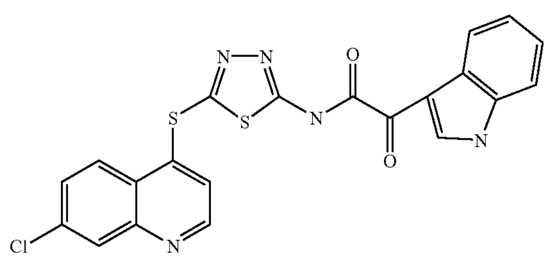 | 466 |
| 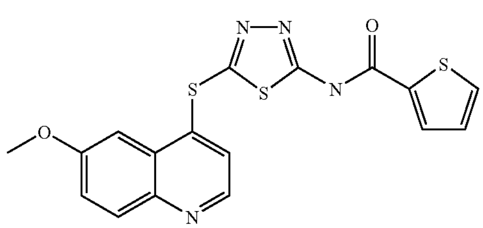 | 401 |

TABLE 2-continued
| Structure | (M + H)+ |
|---|---|
| 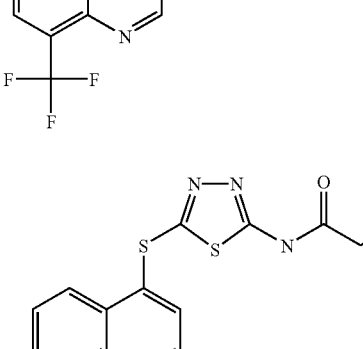 | 439 |
| 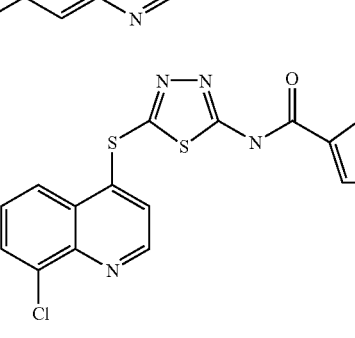 | 365 |
| 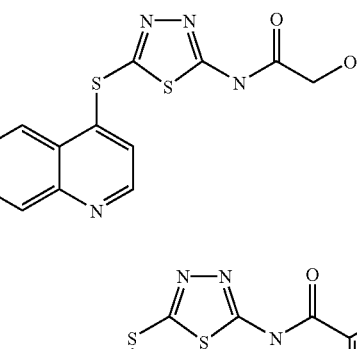 | 405 |
| 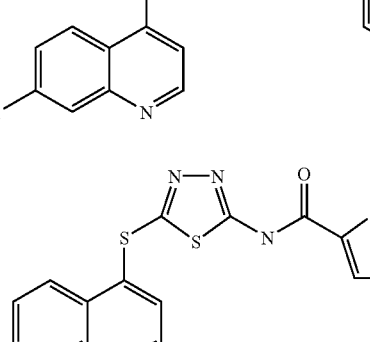 | 429 |
| 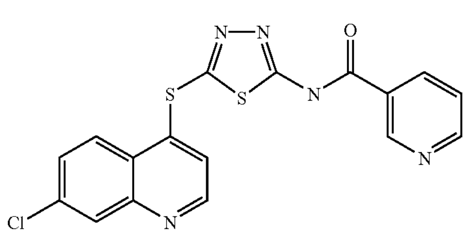 | 400 |
| 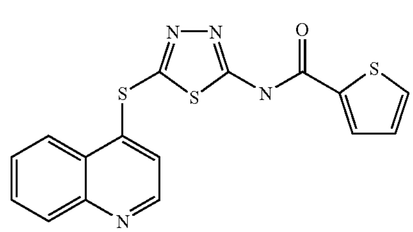 | 371 |

TABLE 2-continued

| Structure | (M + H)+ |
|---|---|
| [7-(trifluoromethyl)quinolin-4-yl-thio-thiadiazole-thiophene-2-carboxamide] | 439 |
| [6-bromoquinolin-4-yl-thio-thiadiazole-thiophene-2-carboxamide] | 550 |
| [5,7-bis(trifluoromethyl)quinolin-4-yl-thio-thiadiazole-thiophene-2-carboxamide] | 507 |
| [ethyl 4-(thiadiazolyl-thio)quinoline-3-carboxylate-thiophene-2-carboxamide] | 443 |
| [6-fluoroquinolin-4-yl-thio-thiadiazole-thiophene-2-carboxamide] | 389 |
| [8-fluoroquinolin-4-yl-thio-thiadiazole-thiophene-2-carboxamide] | 389 |

TABLE 2-continued
| Structure | (M + H)+ |
|---|---|
| 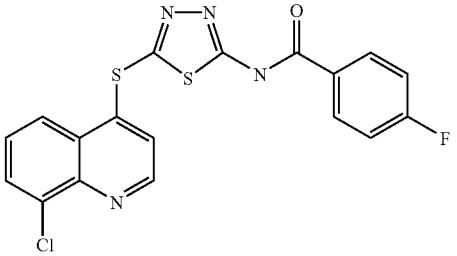 | 417 |
| 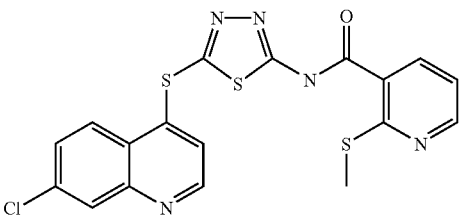 | 446 |
| 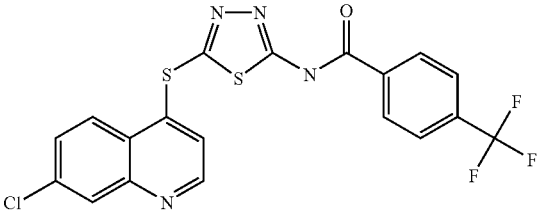 | 467 |
| 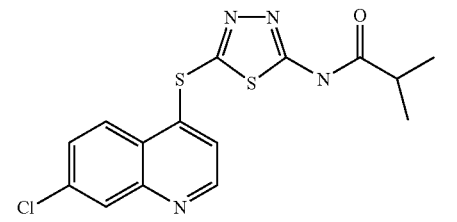 | 365 |
| 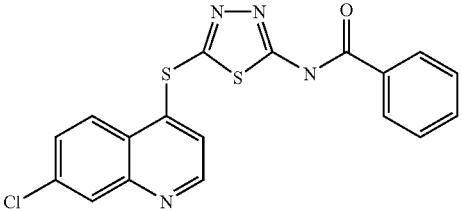 | 399 |
| 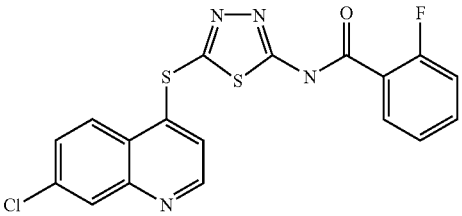 | 417 |

TABLE 2-continued
| Structure | (M + H)+ |
|---|---|
| 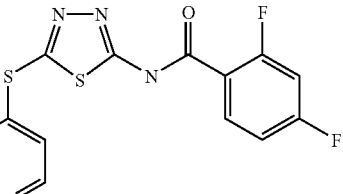 | 435 |
| 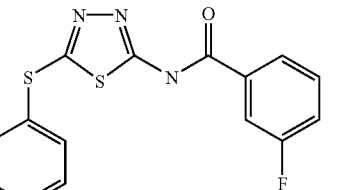 | 417 |
| 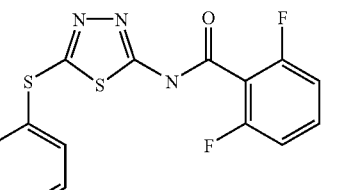 | 435 |
| 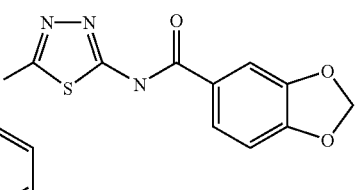 | 443 |
| 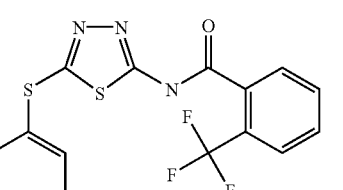 | 467 |
| 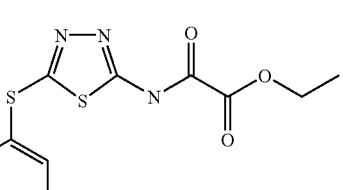 | 395 |
| 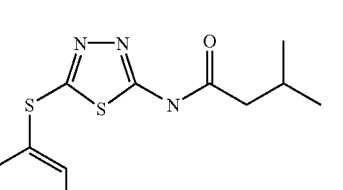 | 379 |

TABLE 2-continued
| Structure | (M + H)+ |
|---|---|
| 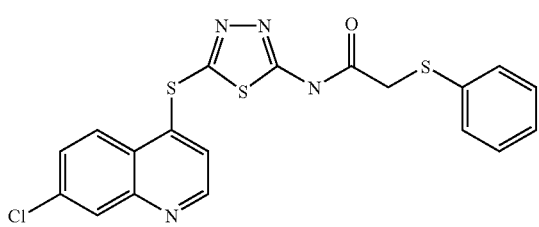 | 445 |
| 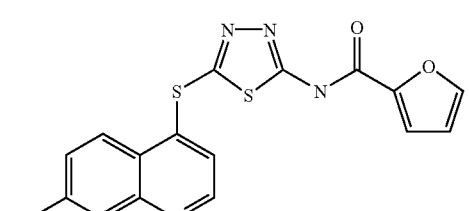 | 389 |
| 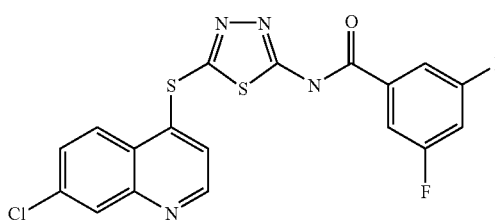 | 435 |
| 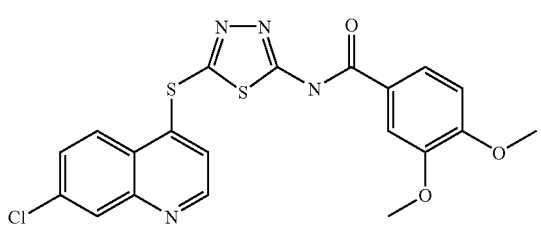 | 459 |
| 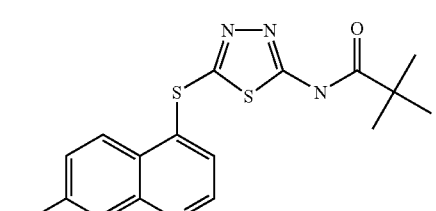 | 379 |
| 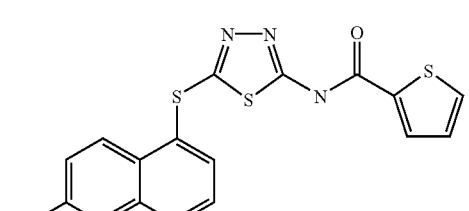 | 405 |

TABLE 2-continued

| Structure | (M + H)+ |
|---|---|
| | 395 |
| 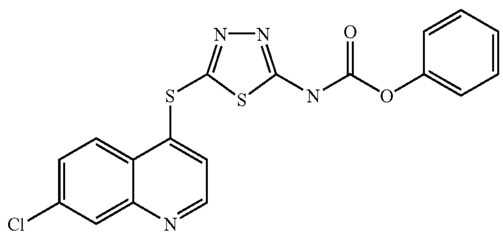 | 415 |
| | 395 |
| | 448 |
| 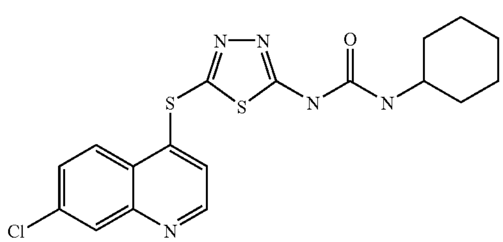 | 420 |
| | 448 |

TABLE 2-continued

| Structure | (M + H)+ |
|---|---|
| 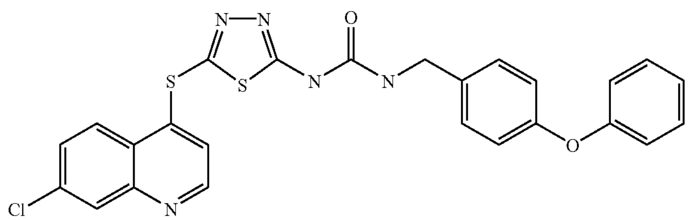 | 520 |
| 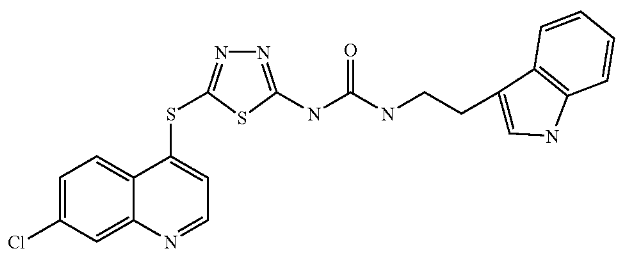 | 481 |
| 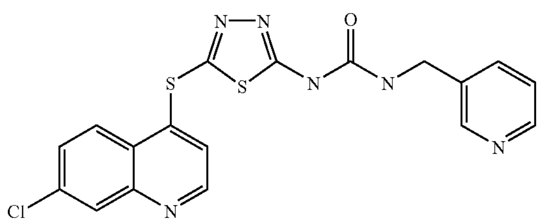 | 429 |
| 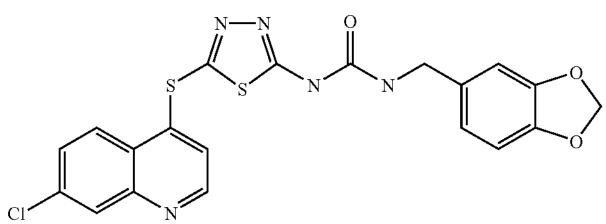 | 472 |
| 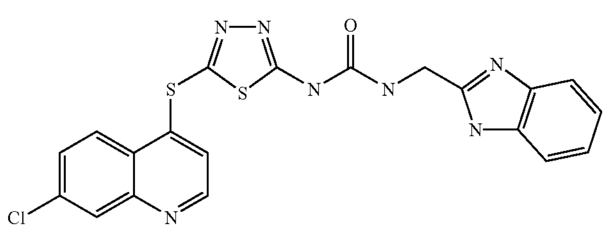 | 468 |
| 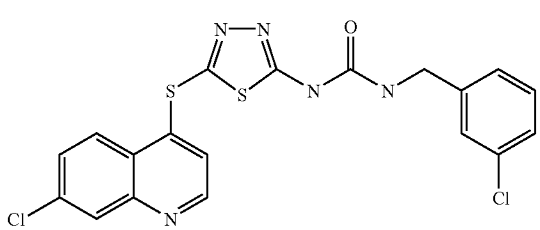 | 462 |

TABLE 2-continued
| Structure | (M + H)+ |
|---|---|
| 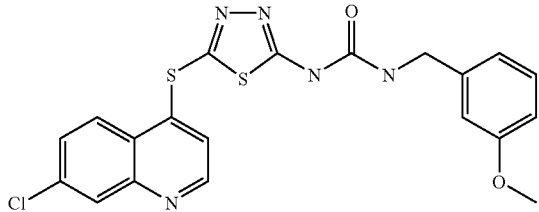 | 458 |
| 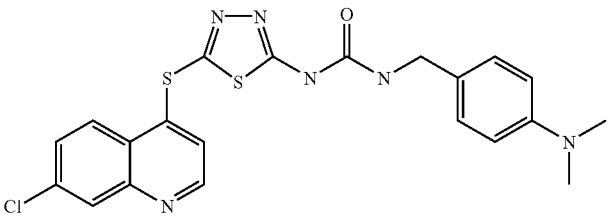 | 471 |
| 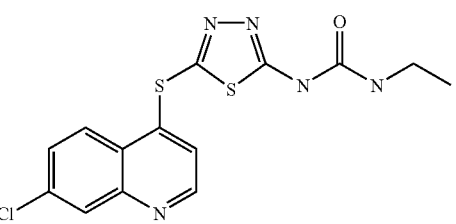 | 366 |
| 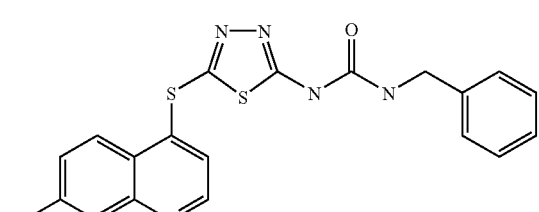 | 428 |
| 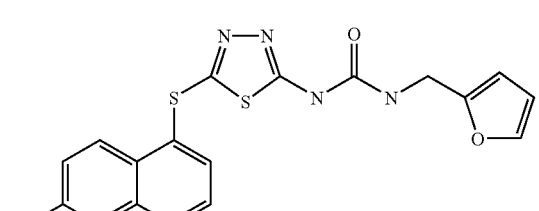 | 418 |
| 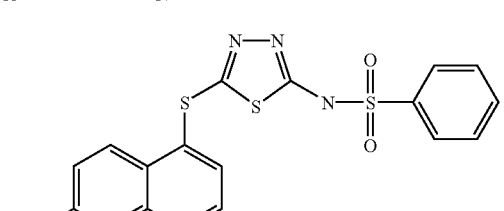 | 435 |
| 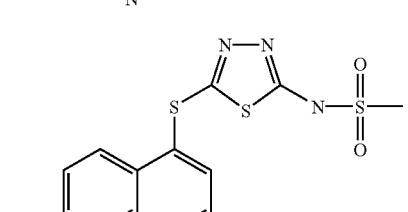 | 373 |

TABLE 2-continued

| Structure | (M + H)+ |
|---|---|
| [7-chloroquinolin-4-yl sulfanyl-thiadiazole-N-methylamine] | 309 |
| [7-chloroquinolin-4-yl sulfanyl-thiadiazole-N-cyclohexylamine] | 381 |
| [7-chloroquinolin-4-yl sulfanyl-thiadiazole-N-phenylamine] | 3.71 |
| [7-chloroquinolin-4-yl sulfanyl-thiadiazole-N-(2-methoxyphenyl)amine] | 401 |
| [7-chloroquinolin-4-yl sulfanyl-thiadiazole-N-(3-methoxyphenyl)amine] | 401 |

JAK Inhibition Assay

Compound inhibition of JAK was assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), was added 2 μM ATP, 5 mM MgCl$_2$, and a solution of compound in DMSO. The reaction was started with JAK enzyme and the plates incubated for 60 minutes at 30° C. The plates were then washed with PBST, 100 μL HRP-Conjugated 4G10 antibody was added, and the plate incubated for 90 minutes at 30° C. The plate was again washed with PBST, 100 μL TMB solution is added, and the plates were incubated for another 30 minutes at 30° C. Sulfuric acid (100 μL of IM) was added to stop the reaction and the plate is read at 450 nm to obtain the optical densities for analysis to determine IC$_{50}$ values.

Certain compounds of the present invention (including those depicted in Table 1) were tested in the above assay for JAK inhibition and were found to have an IC$_{50}$ of less than 2 μM.

Certain other compounds of the present invention (including those depicted in Table 1) were tested in the above assay for JAK inhibition and were found to have an $IC_{50}$ of between 2 and 5 μM.

What is claimed is:

1. A compound of formula I:

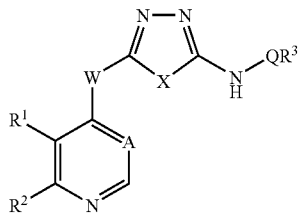

or a pharmaceutically acceptable salt thereof, wherein:

W and X are each independently oxygen or sulfur;

A is nitrogen, CH, C—CN, or C—($C_{1-3}$ aliphatic);

$R^1$ and $R^2$ are taken together to form an optionally substituted 3-7 membered saturated, partially unsaturated, or fully unsaturated ring having 0-3 heteroatoms independently selected from nitrogen, oxygen, or sulfur;

Q is —C(O)—, —C(O)NR—, —C(O)C(O)—, —$CO_2$—, —C(O)$CO_2$—, —$SO_2$—, or an optionally substituted $C_{1-6}$ alkylidene chain, wherein:
one or two non-adjacent methylene units of Q are optionally and independently replaced by —O—, —S—, —NR—, —C(O)—, —$CO_2$—, —C(O)NR—, —OC(O)NR—, —NRC(O)—, NR$CO_2$—, —NRC(O)NR—, —S(O)—, —$SO_2$—, —NR$SO_2$—, —$SO_2$NR—, or —NR$SO_2$NR—;

each R is independently hydrogen or an optionally substituted $C_{1-6}$ aliphatic group, wherein:
two R bound to the same nitrogen atom are optionally taken together with the nitrogen to form an optionally substituted 3-7 membered saturated, partially unsaturated, or fully unsaturated ring having 0-2 heteroatoms, in addition to the nitrogen bound thereto, independently selected from nitrogen, oxygen, or sulfur;

$R^3$ is Ar; and

Ar is an optionally substituted ring selected from:
(a) a 3-8 membered monocyclic or 8-10 membered bicyclic carbocyclic saturated, partially unsaturated, or aryl ring; or
(b) a 5-6 membered monocyclic or 8-10 membered bicyclic heteroaryl ring having 1-4 heteroatoms independently selected from nitrogen, oxygen, or sulfur, provided that said compound is not a compound selected from the group consisting of:

3-Chloro-benzo[b]thiophene-2-carboxylic acid [5-(7-chloro-quinolin-4-ylsulfanyl)-[1,3,4]thiadiazol-2-yl]-amide;

N-[5-(7-Chloro-quinolin-4-ylsulfanyl)-[1,3,4]thiadiazol-2-yl]-2-phenoxy-nicotinamide;

5-Methyl-2-phenyl-2H-[1,2,3]triazole-4-carboxylic acid [5-(7-chloro-quinolin-4-ylsulfanyl)-[1,3,4]thiadiazol-2-yl]-amide;

Cyclopropanecarboxylic acid [5-(7-chloro-quinolin-4-yl-sulfanyl)-[1,3,4]thiadiazol-2-yl]-amide;

Thiophene-2-carboxylic acid [5-(7-chloro-quinolin-4-yl-sulfanyl)-[1,3,4]thiadiazol-2-yl]-amide; and 4-Hydroxy-2-oxo-2,3-dihydro-quinoline-3-carboxylic acid [5-(7-chloro-quinolin-4-ylsulfanyl)-[1,3,4]thiadiazol-2-yl]-amide.

2. The compound according to claim 1, wherein:
$R^1$ and $R^2$ are taken together to form an optionally substituted 5-7 membered saturated, partially unsaturated, or fully unsaturated ring having 0-2 heteroatoms independently selected from nitrogen, oxygen, or sulfur.

3. The compound according to claim 2, wherein:
$R^1$ and $R^2$ are taken together to form an optionally substituted benzo, thieno, cyclohexo, pyrido, tetrahydropyrido, or pyrimido ring.

4. The compound according to claim 1, wherein:
Q is —C(O)—, —C(O)NR—, —$CO_2$—, —C(O)$CO_2$—, —$SO_2$—, or an optionally substituted $C_{1-4}$ alkylidene chain wherein:
one or two non-adjacent methylene units of Q are optionally and independently replaced by —O—, —S—, —NR—, —C(O)—, —$CO_2$—, or —$SO_2$—.

5. The compound according to claim 1, wherein:
$R^3$ is an optionally substituted ring selected from:
(a) a 3-6 membered monocyclic carbocyclic saturated or aryl ring; or
(b) a 5-6 membered monocyclic or a 9-10 membered bicyclic heteroaryl ring having 1-3 heteroatoms independently selected from nitrogen, oxygen, or sulfur.

6. The compound according to claim 5, wherein:
$R^3$ is an optionally substituted group selected from cyclopropyl, cyclopentyl, cyclohexyl, phenyl, pyridyl, thienyl, furanyl, isoxazolyl, triazolyl, benzothienyl, or benzo[1,3]dioxolyl.

7. The compound according to any one of claims 1-6, wherein W is sulfur.

8. The compound according to claim 7, wherein X is sulfur.

9. The compound according to claim 8, wherein A is nitrogen.

10. The compound according to claim 8, wherein A is CH.

11. A compound selected from the following compounds:

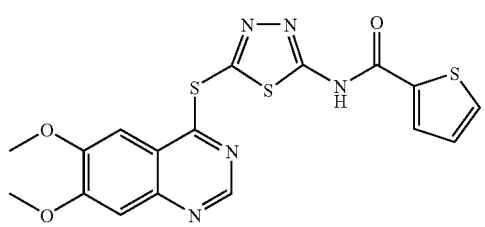

I-2

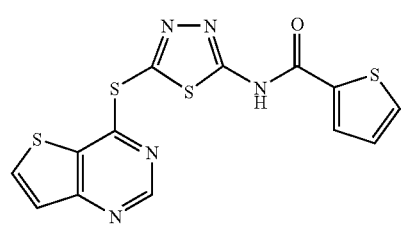

I-3

I-4
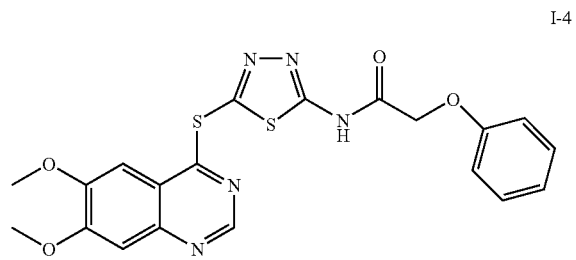
I-5
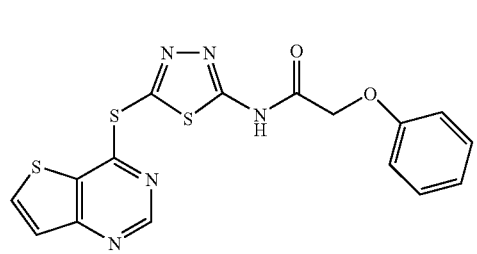
I-7
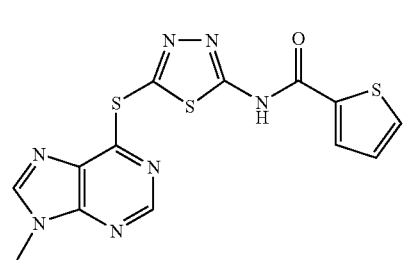
I-8
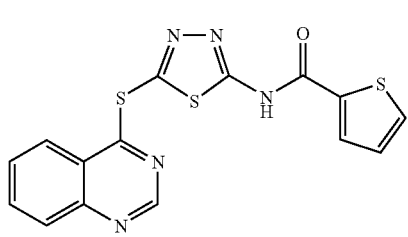
I-9
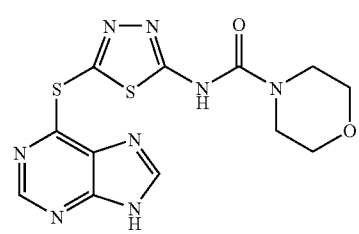
I-10
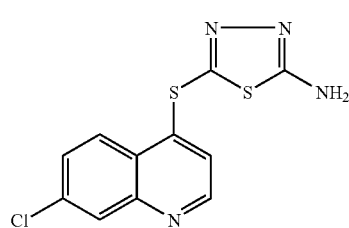
I-13
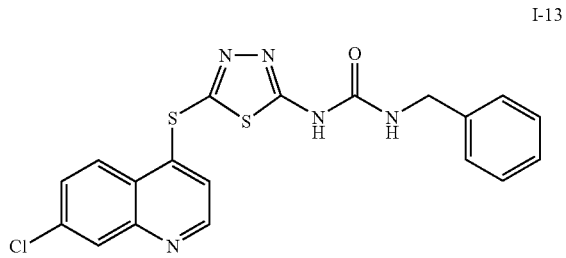
I-14
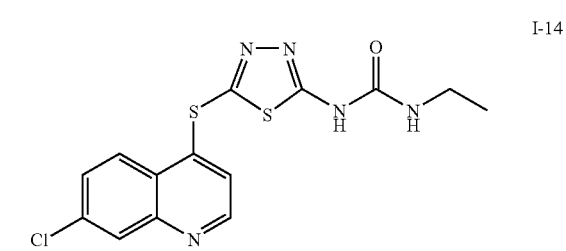
I-15
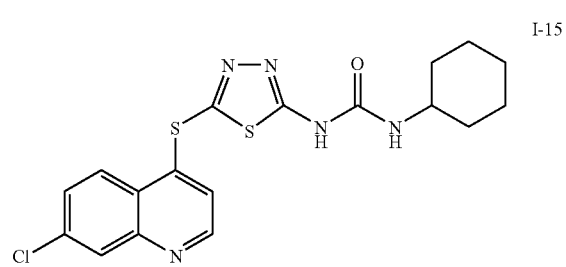
I-16
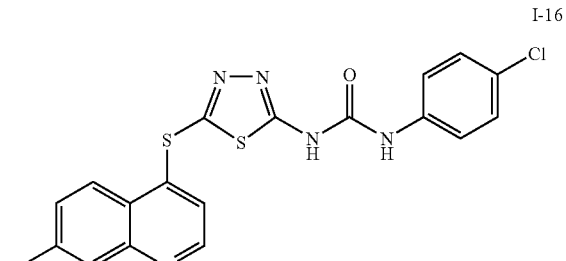
I-17
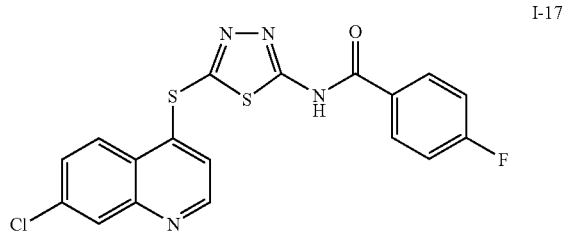
I-18
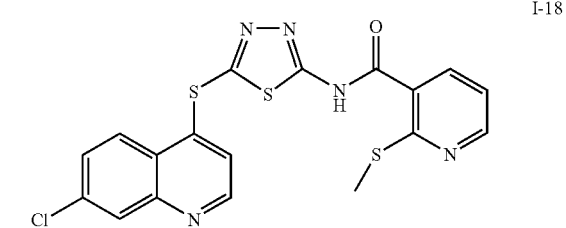

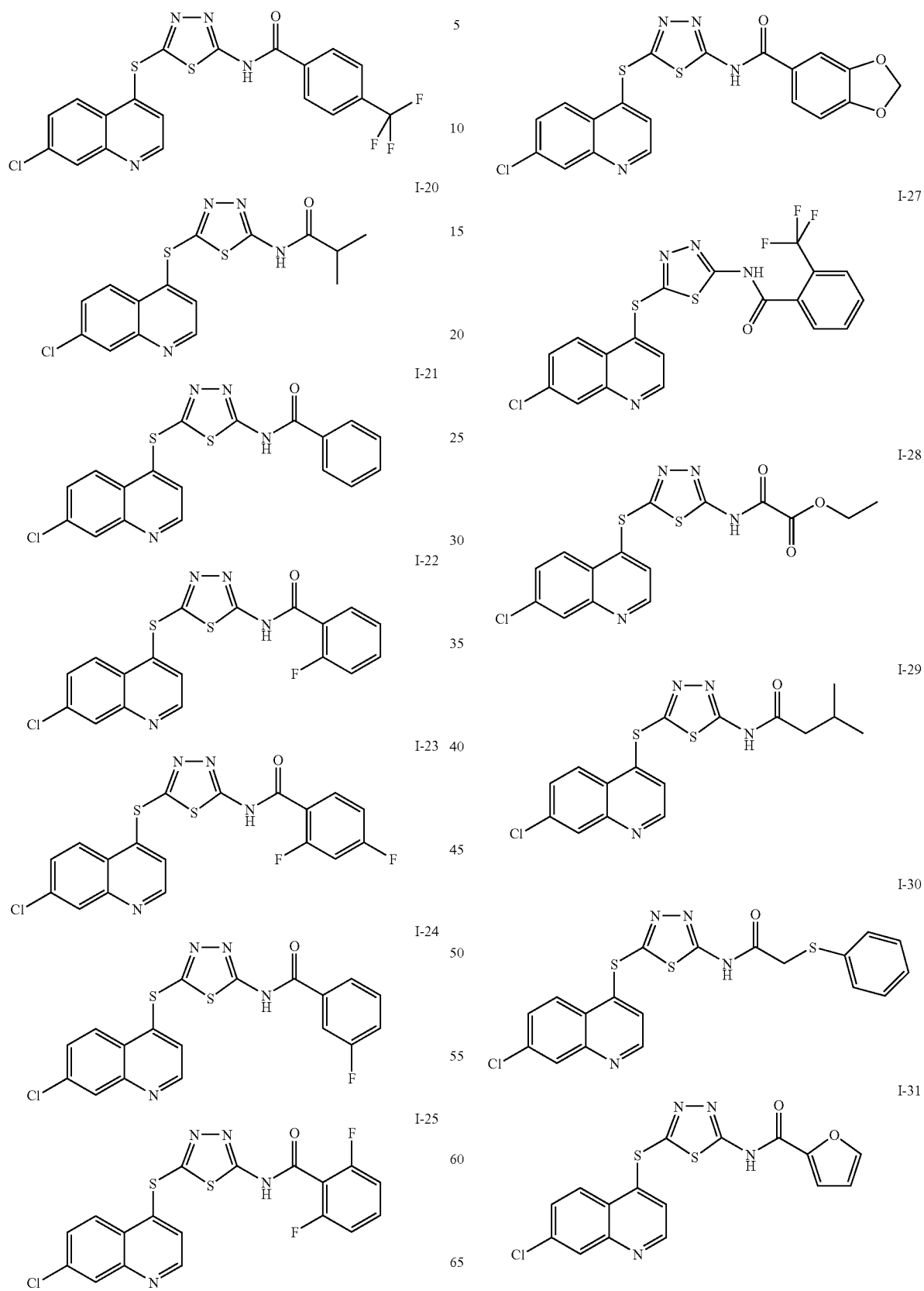

-continued
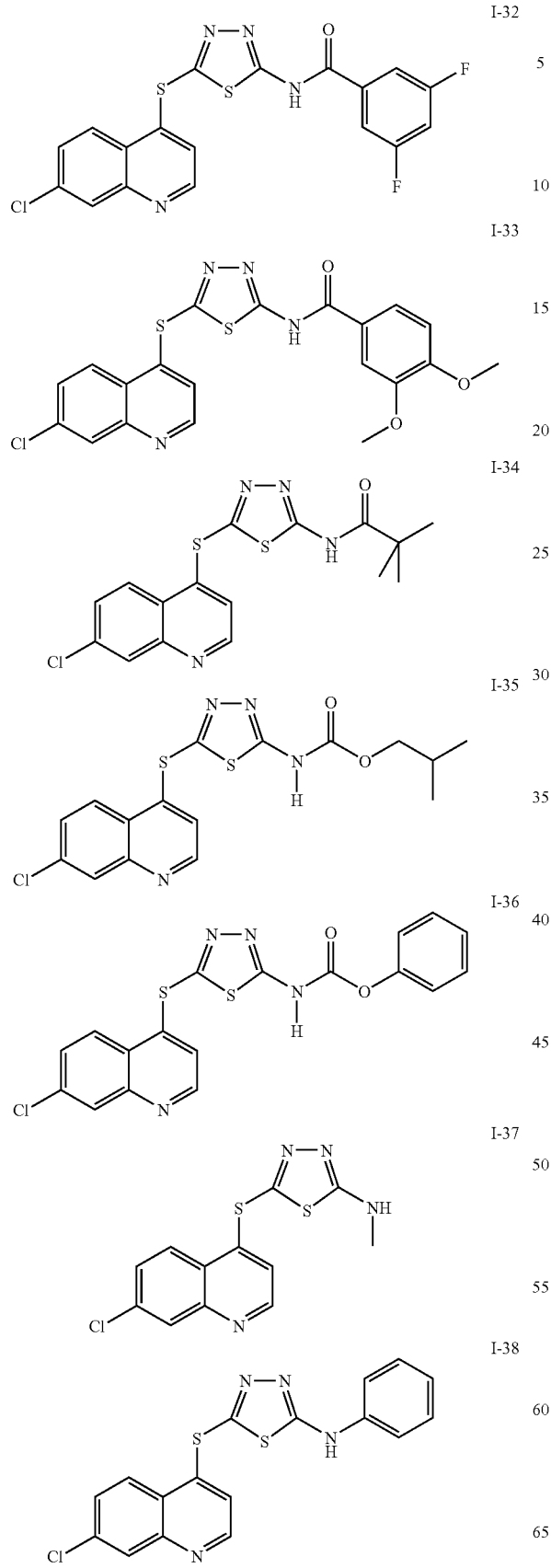
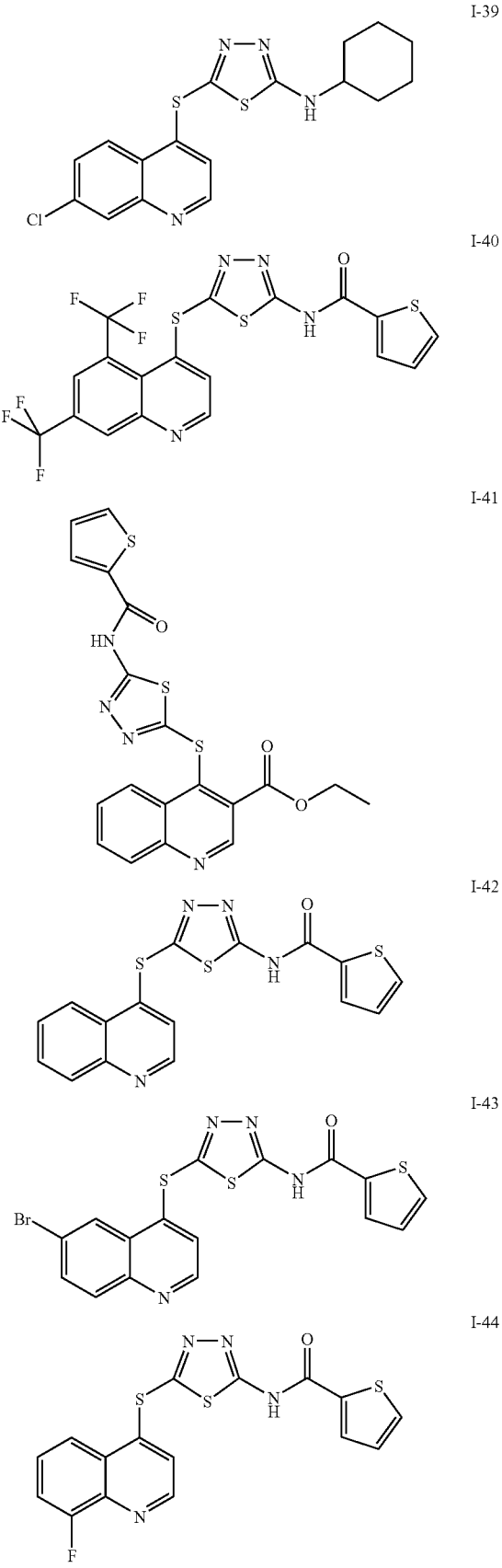

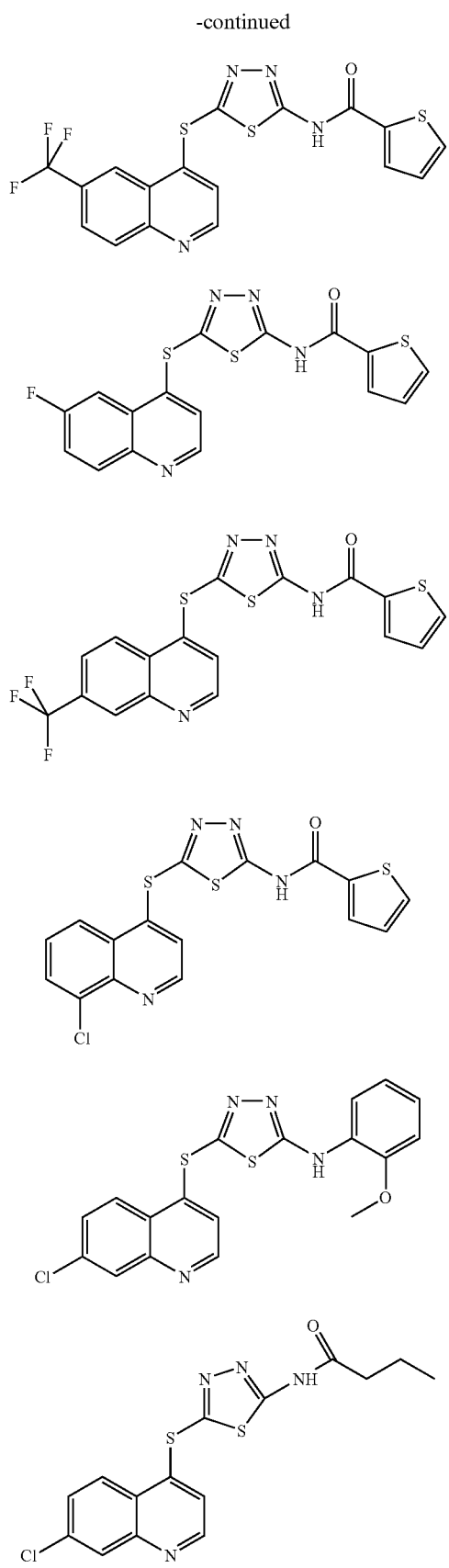
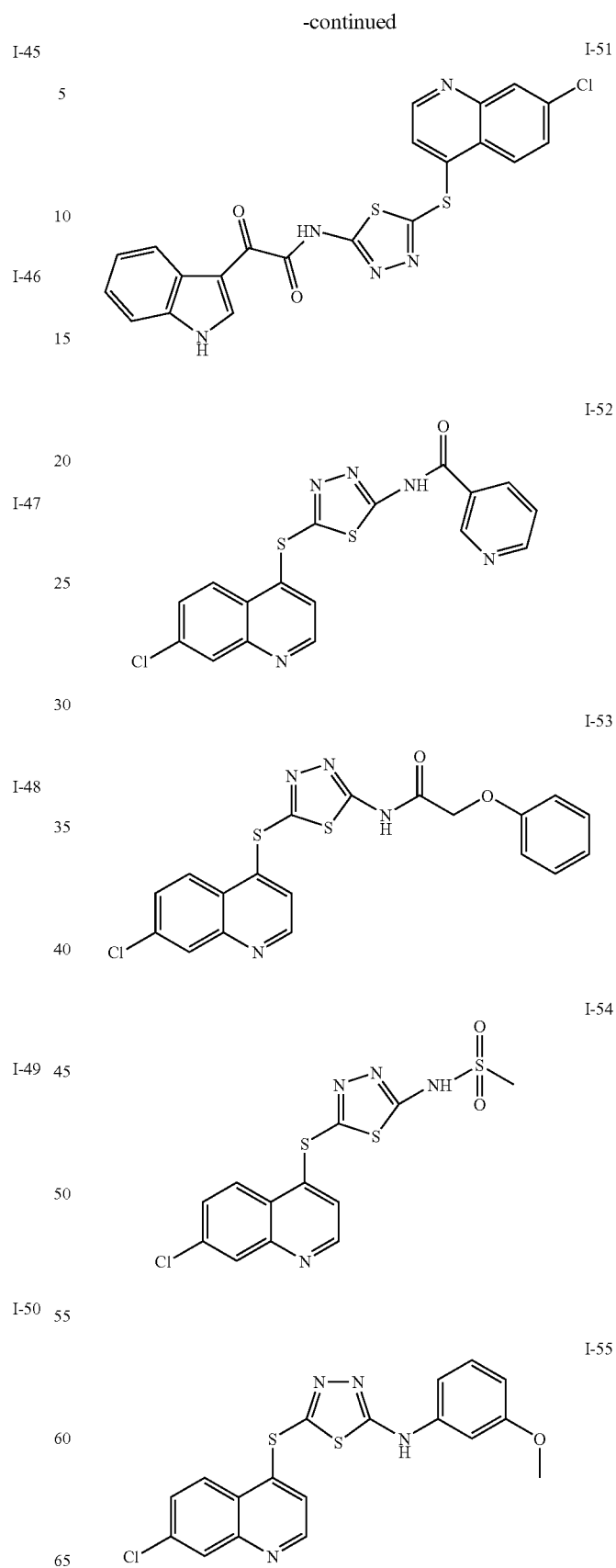

-continued
I-56
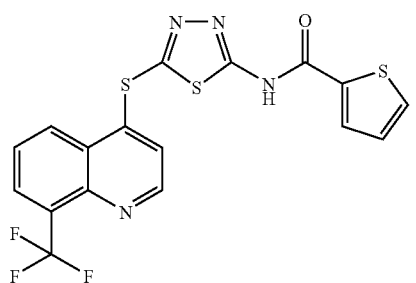
I-57
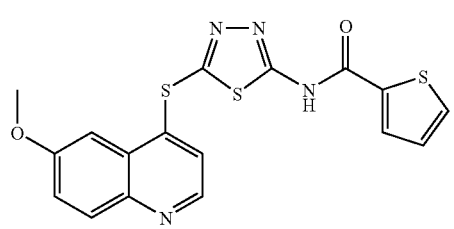
I-58
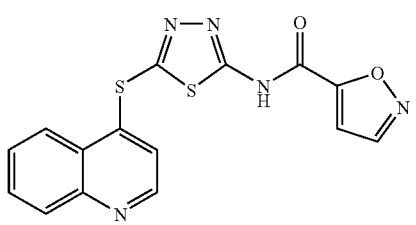
I-59
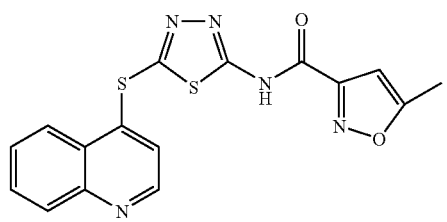
I-60
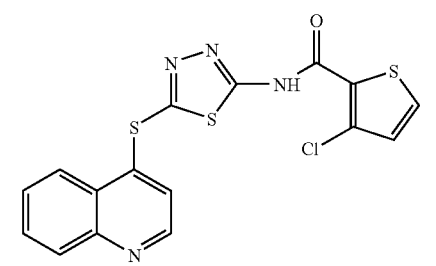
I-61
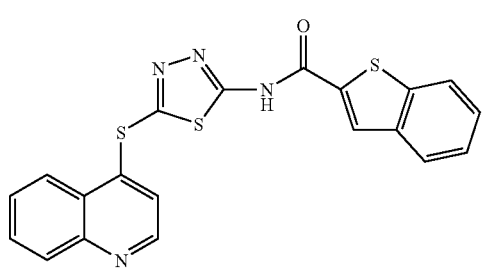
-continued
I-62
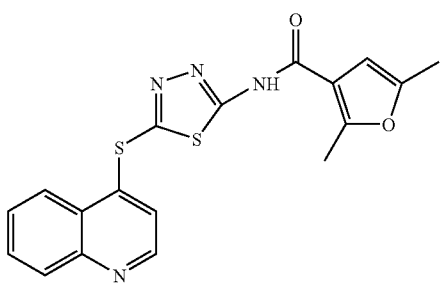
I-63
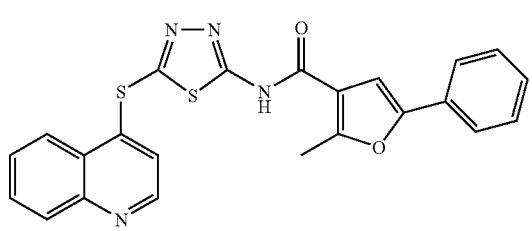
I-64
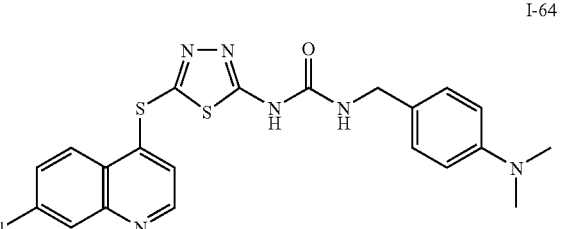
I-65
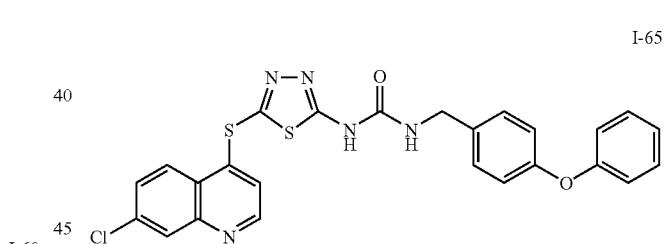
I-66
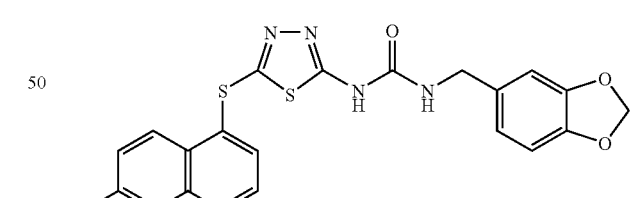
I-67
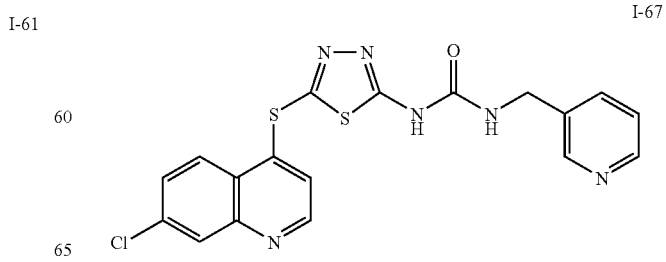

-continued
I-68
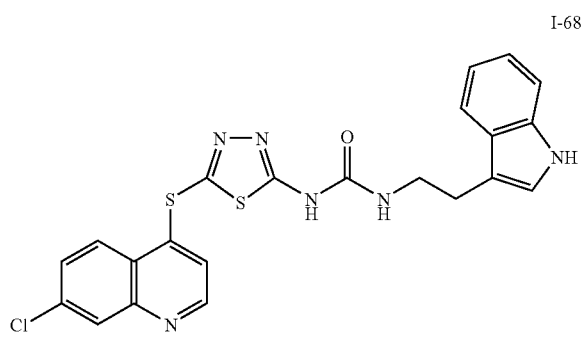
I-69
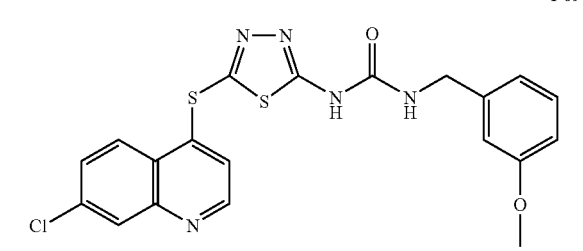
I-70
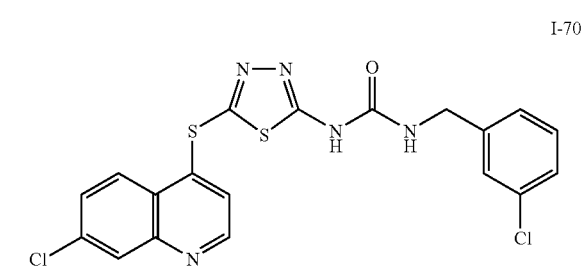
I-71
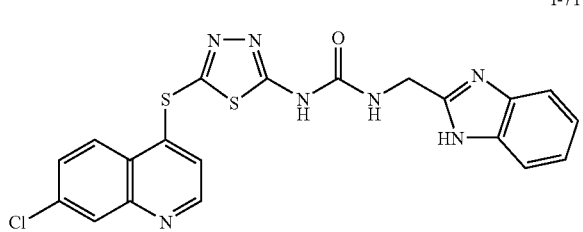
I-72
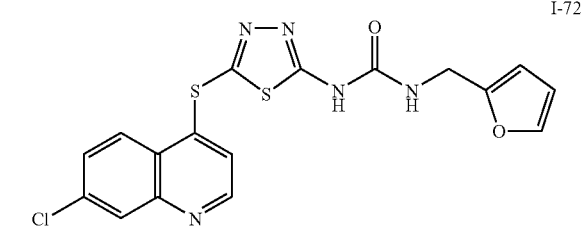
I-73
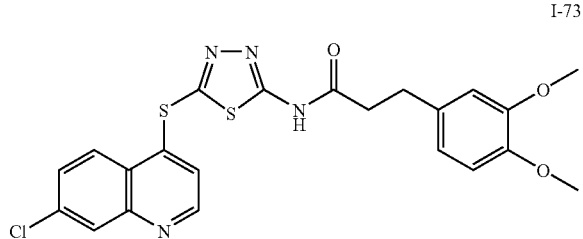
-continued
I-78
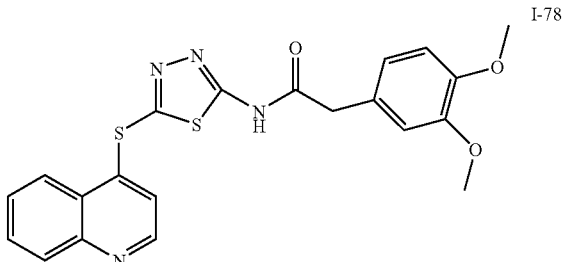
I-79
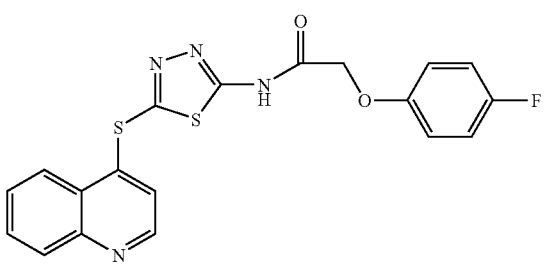
I-80
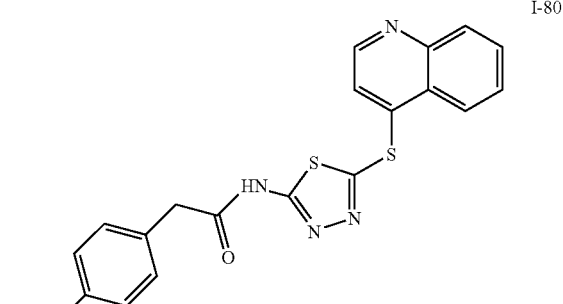
I-81
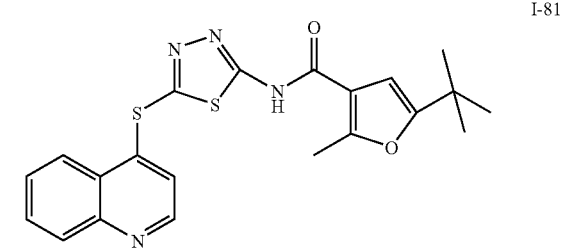
I-82
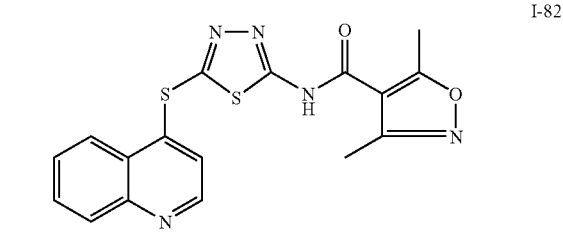
I-83
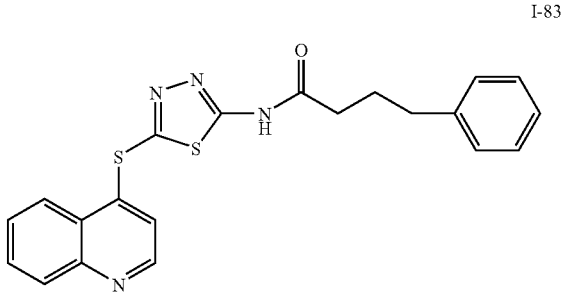

-continued

I-84

I-85

I-86

I-87

I-88

I-89

-continued

I-90

I-91

I-92

I-93

I-94

I-95

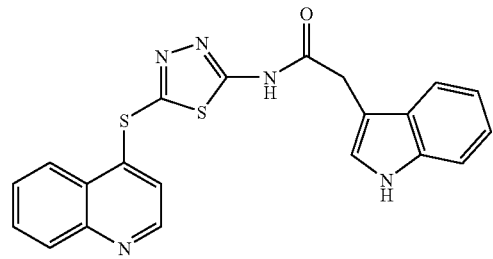
I-96
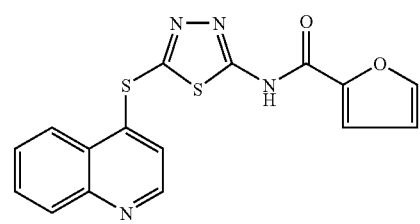
I-97
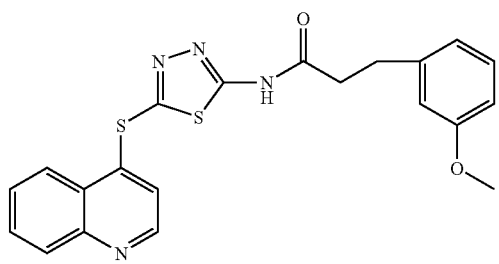
I-98
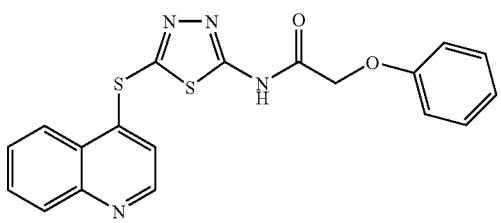
I-99
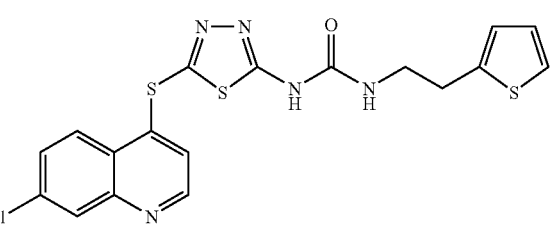
I-100
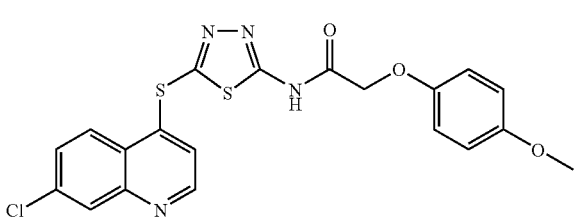
I-101
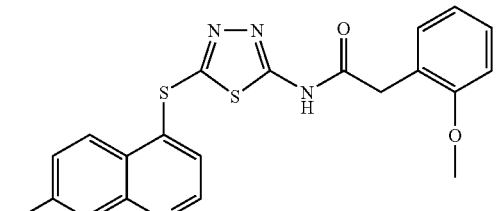
I-102
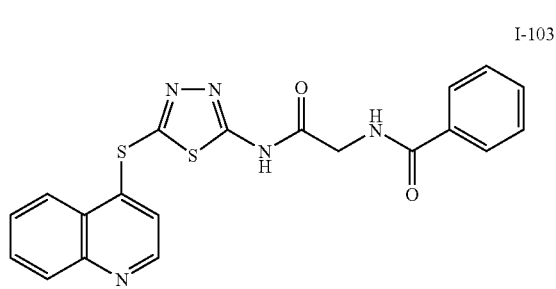
I-103
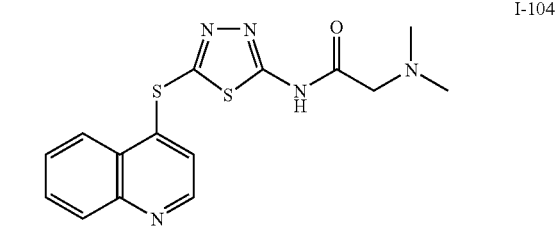
I-104
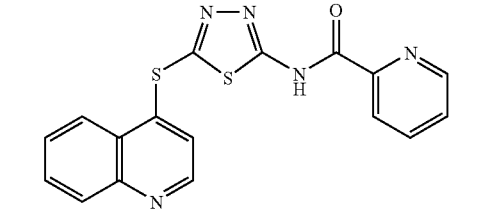
I-105
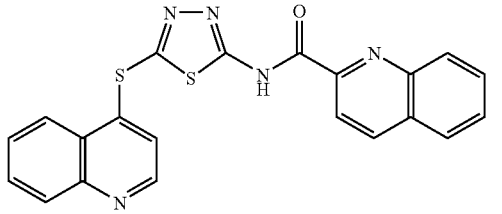
I-106
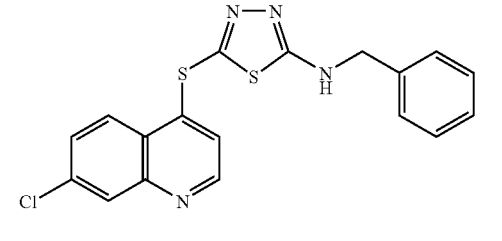
I-107

-continued

I-108
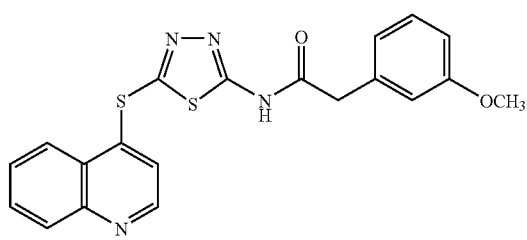

I-109
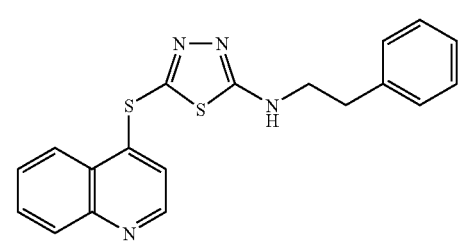

I-110
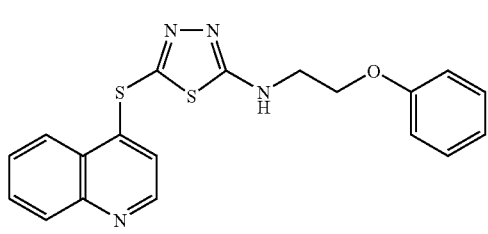

I-111
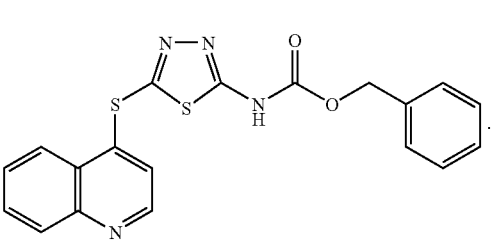

12. A composition comprising an effective amount of a compound according to claim 1, or a pharmaceutically acceptable salt thereof, and a pharmaceutically acceptable carrier, adjuvant, or vehicle.

13. The composition according to claim 12, wherein:

$R^1$ and $R^2$ are taken together to form an optionally substituted 5-7 membered saturated, partially unsaturated, or fully unsaturated ring having 0-2 heteroatoms independently selected from nitrogen, oxygen, or sulfur.

14. The composition according to claim 12, wherein:

Q is —C(O)—, —C(O)NR—, —CO$_2$—, —C(O)CO$_2$—, —SO$_2$—, or an optionally substituted $C_{1-4}$ alkylidene chain wherein:

one or two non-adjacent methylene units of Q are optionally and independently replaced by —O—, —S—, —NR—, —C(O)—, —CO$_2$—, or —SO$_2$—.

15. The composition according to claim 12, wherein:

$R^3$ is an optionally substituted ring selected from:

(a) a 3-6 membered monocyclic carbocyclic saturated or aryl ring; or (b) a 5-6 membered monocyclic or a 9-10 membered bicyclic heteroaryl ring having 1-3 heteroatoms independently selected from nitrogen, oxygen, or sulfur.

16. The composition according to any one of claims 12-15, wherein W is sulfur.

17. The composition according to claim 16, wherein X is sulfur.

18. The composition according to claim 16, wherein A is nitrogen.

19. The composition according to claim 16, wherein A is CH.

20. The composition according to claim 12, additionally comprising an additional therapeutic agent selected from an anti-proliferative agent, an anti-inflammatory agent, an immunomodulatory agent, a neurotrophic factor, or an agent for treating cardiovascular disease.

21. A composition comprising a compound according to claim 11, and a pharmaceutically acceptable carrier, adjuvant, or vehicle.

* * * * *